US008934092B2

(12) United States Patent
Oshima et al.

(10) Patent No.: US 8,934,092 B2
(45) Date of Patent: Jan. 13, 2015

(54) SURFACE DEFECT INSPECTION METHOD AND APPARATUS

(71) Applicants: Yoshimasa Oshima, Tokyo (JP); Toshiyuki Nakao, Tokyo (JP); Shigeru Matsui, Tokyo (JP)

(72) Inventors: Yoshimasa Oshima, Tokyo (JP); Toshiyuki Nakao, Tokyo (JP); Shigeru Matsui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 178 days.

(21) Appl. No.: 13/838,460

(22) Filed: Mar. 15, 2013

(65) Prior Publication Data

US 2013/0208271 A1  Aug. 15, 2013

Related U.S. Application Data

(63) Continuation of application No. 13/221,314, filed on Aug. 30, 2011, now Pat. No. 8,400,629, which is a continuation of application No. 12/727,752, filed on Mar. 19, 2010, now Pat. No. 8,035,808, which is a continuation of application No. 12/109,548, filed on Apr. 25, 2008, now Pat. No. 7,710,557.

(30) Foreign Application Priority Data

Apr. 25, 2007  (JP) ................................. 2007-115004
Jun. 13, 2007  (JP) ................................. 2007-156385

(51) Int. Cl.
*G01N 21/00* (2006.01)
*G01N 21/88* (2006.01)

(52) U.S. Cl.
USPC .................................. 356/237.5; 250/559.45

(58) Field of Classification Search
None
See application file for complete search history.

(56) References Cited

U.S. PATENT DOCUMENTS

| | | | |
|---|---|---|---|
| 5,377,001 A | 12/1994 | Malin et al. | |
| 5,377,002 A | 12/1994 | Malin et al. | |
| 5,903,342 A | 5/1999 | Yatsugake et al. | |
| 6,654,111 B2 | 11/2003 | Isozaki et al. | |
| 6,731,384 B2 | 5/2004 | Oshima et al. | |
| 6,894,302 B2 | 5/2005 | Ishimaru et al. | |
| 7,106,432 B1 | 9/2006 | Mapoles et al. | |
| 7,110,106 B2 | 9/2006 | Xu et al. | |
| 7,154,597 B2 | 12/2006 | Miyakawa et al. | |
| 7,286,218 B2 | 10/2007 | Tiemeyer et al. | |
| 7,369,223 B2 | 5/2008 | Hamamatsu et al. | |
| 7,417,722 B2 | 8/2008 | Bills et al. | |
| 7,433,031 B2 | 10/2008 | Xu et al. | |
| 7,492,452 B2 | 2/2009 | Uto et al. | |
| 7,528,942 B2 | 5/2009 | Nakano et al. | |

(Continued)

FOREIGN PATENT DOCUMENTS

EP           524348 A1    1/1993
JP         62-011151      1/1987

(Continued)

*Primary Examiner* — Gordon J Stock, Jr.
(74) *Attorney, Agent, or Firm* — Antonelli, Terry, Stout & Kraus, LLP.

(57) ABSTRACT

A surface defect inspection apparatus and method for irradiating a beam multiple times to a same region on a surface of an inspection sample, detecting each scattered light from the same region by detection optical systems individually to produce plural signals, and wherein irradiating the beam includes performing a line illumination of the beam on a line illumination region of the sample surface. The line illumination region is moved in a longitudinal direction at a pitch shorter than a length of the line illumination region in the longitudinal direction.

14 Claims, 21 Drawing Sheets

(56) References Cited

U.S. PATENT DOCUMENTS

| | | |
|---|---|---|
| 7,557,913 B2 | 7/2009 | Otani et al. |
| 7,664,608 B2 | 2/2010 | Urano et al. |
| 7,710,557 B2 | 5/2010 | Oshima et al. |
| 8,035,808 B2 | 10/2011 | Oshima et al. |
| 2003/0011760 A1 | 1/2003 | Vaez-Iravani et al. |
| 2003/0193666 A1 | 10/2003 | Abraham et al. |
| 2006/0250612 A1 | 11/2006 | Meeks |
| 2006/0290923 A1 | 12/2006 | Nakano et al. |
| 2007/0182958 A1 | 8/2007 | Manabe et al. |
| 2012/0019835 A1* | 1/2012 | Nakao et al. .................. 356/600 |
| 2012/0092656 A1* | 4/2012 | Nakao et al. ................ 356/237.3 |
| 2012/0133928 A1* | 5/2012 | Urano et al. ................ 356/237.2 |
| 2012/0194807 A1* | 8/2012 | Maruyama et al. ......... 356/237.2 |
| 2012/0314211 A1* | 12/2012 | Ando et al. ................. 356/237.2 |
| 2013/0003052 A1* | 1/2013 | Nakao et al. ................ 356/237.5 |

FOREIGN PATENT DOCUMENTS

| | | |
|---|---|---|
| JP | 9-304289 | 11/1997 |
| JP | 2000-162141 | 6/2000 |
| JP | 2001-255278 | 9/2001 |
| JP | 2002-277399 | 9/2002 |
| JP | 2005-283190 | 10/2005 |
| JP | 2005-345221 | 12/2005 |
| JP | 2007-033433 | 2/2007 |

* cited by examiner

US 8,934,092 B2

SURFACE DEFECT INSPECTION METHOD AND APPARATUS

CROSS-REFERENCE TO RELATED APPLICATIONS

This application is a continuation of U.S. application Ser. No. 13/221,314, filed Aug. 30, 2011, which, in turn, is a continuation of U.S. application Ser. No. 12/727,752, filed Mar. 19, 2010 (now U.S. Pat. No. 8,035,808), which, in turn, is a continuation of U.S. application Ser. No. 12/109,548, filed Apr. 25, 2008 (now U.S. Pat. No. 7,710,557), and which application claims priority from Japanese Application JP 2007-115004 filed on Apr. 25, 2007 and Japanese Application JP 2007-156385 filed on Jun. 13, 2007, the contents of which are hereby incorporated by reference into this application.

BACKGROUND OF THE INVENTION

Field of the Invention

The present invention relates to a surface defect inspection method and a surface defect inspection apparatus for detecting a tiny foreign matter/defect on the surface of the semiconductor substrate and the like with high sensitivity at high speeds.

On the manufacturing line of the semiconductor substrate or the thin film substrate, the inspection with respect to the defect and foreign matter on the surface of the semiconductor substrate or the thin film substrate is performed for the purpose of maintaining and further improving the product yield. For example, the sample of the semiconductor substrate prior to formation of the circuit pattern requires detection of the tiny defect or foreign matter with the size equal to or smaller than 0.05 µm on the surface. It is essential to periodically inspect whether or not the tiny defect or the foreign matter exists in the respective step of the manufacturing facility in order to improve the production yield.

The generally employed inspection apparatus as disclosed in JP-A 9-304289 and 2000-162141, and U.S. Pat. No. 5,903,342 is structured to irradiate the laser beam of several tens µm focused on the surface of the sample so as to condense and detect the scattered light from the defect or the foreign matter. With the art for classifying the defect type has been disclosed in Japanese Unexamined Patent Application Publication No. 2001-255278 or U.S. Pat. No. 6,894,302, the scattered light from the defect is multi-directionally detected so as to identify the directionality of the scattered light.

SUMMARY OF THE INVENTION

A problem to be solved by the present invention will be described. The distribution of the scattered light caused by the defect with the size corresponding to 1/10 of the illumination wavelength becomes isotropic. So the SN ratio is improved by adding the multi-directionally detected signals, which makes it possible to detect the tiny defect. Meanwhile, the defect which causes the distribution of the scattered light to be anisotropic reduces the SN ratio by adding the multi-directionally detected signals, thus lowering the detection sensitivity. The surface defect inspection with respect to the semiconductor substrate is required to be performed with high sensitivity irrespective of the defect type.

The tiny defect inspection is performed by adding the detection signals of the multi-directionally detected scattered lights, and the respective detected signals are individually processed so as to avoid the error failing to detect the anisotropic defect. The specific structures will be described hereinafter.

According to the first aspect of the structure, in a surface defect inspection apparatus, a laser beam focused on a surface of an inspection sample is irradiated, a scattered light generated on the surface of the inspection sample is multi-directionally condensed, and the condensed scattered light is photoelectrically converted to inspect a defect which exists on the surface of the inspection sample. Multi-directionally detected detection signals are added to detect a tiny defect. Each of the multi-directionally detected detection signals is individually processed to detect an anisotropic defect.

According to the second aspect of the structure, in a surface defect inspection apparatus, a laser beam focused on a surface of an inspection sample is irradiated, a scattered light generated on the surface of the inspection sample is multi-directionally condensed, and the condensed scattered light is photoelectrically converted to inspect a defect which exists on the surface of the inspection sample. The apparatus includes first plural photoelectric conversion elements for performing a multi-directional detection, and second plural photoelectric conversion elements for performing the multi-directional detection. The first plural photoelectric conversion elements are arranged each at a first elevation angle with respect to an inspection sample surface, and the second plural photoelectric conversion elements are arranged each at a second elevation angle higher than the first elevation angle.

According to the third aspect of the structure, in a surface defect inspection apparatus, a laser beam focused on a surface of an inspection sample is irradiated, a scattered light generated on the surface of the inspection sample is multi-directionally condensed, and the condensed scattered light is photoelectrically converted to inspect a defect which exists on the surface of the inspection sample. The apparatus includes first plural photoelectric conversion elements for performing a multi-directional detection, and second plural photoelectric conversion elements for performing the multi-directional detection. The first plural photoelectric conversion elements are arranged each at a first elevation angle with respect to an inspection sample surface, the second plural photoelectric conversion elements are arranged each at a second elevation angle higher than the first elevation angle, and sensitivity of the first and the second plural photoelectric conversion elements is individually adjusted.

According to the fourth aspect of the structure, in a surface defect inspection apparatus, a laser beam focused on a surface of an inspection sample is irradiated, a scattered light generated on the surface of the inspection sample is multi-directionally condensed, and the condensed scattered light is photoelectrically converted to inspect a defect which exists on the surface of the inspection sample. The apparatus includes first plural photoelectric conversion elements for performing a multi-directional detection, and second plural photoelectric conversion elements for performing the multi-directional detection. The first plural photoelectric conversion elements are arranged each at a first elevation angle with respect to an inspection sample surface, and the second plural photoelectric conversion elements are arranged each at a second elevation angle higher than the first elevation angle. The first and the second plural photoelectric conversion elements are allowed to set the threshold value capable of distinguishing the detection signal, that is, noise from the defect signal based on the level of the shot noise caused by the photoelectric conversion element.

Another problem to be solved by the present invention will be described. Recently, the LSI wiring has been rapidly miniaturized to cause the size of the defect to be detected in the optical inspection to approach the limit of detection. According to the semiconductor roadmap, in the year 2007, the mass production of the LSI of 65 nm node has reportedly been about to start. The production requires the performance for detecting the defect with the size half the DRAM 1/2 pitch.

It is known that the scattered light intensity I upon the laser irradiation to the defect establishes the relationship of $I \propto d^6$ (d: particle size of the defect). That is, as the defect size becomes smaller, the generated scattered light is rapidly reduced. The process for reducing the illumination wavelength, increasing the output of the laser, reducing the laser beam spot may be employed for intensifying the generated scattered light. The improvement in the detection sensitivity by reducing the wavelength will be described. Assuming that the illumination wavelength is set to $\lambda$, the scattered light intensity I establishes the relationship of $I \propto \lambda^{(-4)}$. In other words, the generated scattered light may be intensified by reducing the illumination wavelength, which is effective for improving the detection sensitivity. However, reduction of the illumination wavelength generally increases the absorbing coefficient of the substance, thus increasing the rate of the temperature rise on the sample surface.

The improvement in the detection sensitivity by increasing the laser output will be described. The scattered light intensity is substantially proportional to the laser output. So the scattered light may be intensified by making the laser output high. Likewise the case for reducing the illumination wavelength, the rate of the temperature rise on the sample surface may be increased. As a result, further improvement in the detection sensitivity to exceed the current level by increasing the output cannot be expected.

The improvement in the detection sensitivity by reducing the illumination spot will be described. Reduction in the illumination spot may reduce the scattered light intensity from the wafer roughness (tiny surface roughness). The detection sensitivity may be improved in view of the noise reduction. However, the laser irradiation per unit area is increased by the reduced beam spot, thus increasing the rate of the temperature rise on the sample surface.

It is difficult for a mere extension of the generally employed process to further improve the detection sensitivity as the sample is damaged by the temperature rise. It is therefore an object of the present invention to provide the surface defect inspection method and the surface defect inspection apparatus for improving the detection sensitivity while suppressing the temperature rise on the sample surface.

In the present invention, the sample is subjected to a line illumination to increase the beam spot length to the feed pitch of the stage such that substantially the same region of the inspection sample is illuminated plural times in the single inspection to add the resultant plural scattered lights for improving the detection sensitivity.

The line illumination may increase the state where two or more defects exist simultaneously in the illumination range. In the aforementioned case, the sensor with the plural pixels may be used for dividing the illumination range so as to individually detect the defects in the respective ranges.

The plural scattered lights resulting from the single inspection are subjected to the appropriate processing such as the amplification and the noise elimination by the analog circuit. Then the scattered lights generated from substantially the same region of the inspection sample are added in the signal processor to improve the sensitivity of the defect detection.

The summary of the present invention for solving the aforementioned problems will be described hereinafter.

(1) A surface defect inspection method includes a step of irradiating a laser beam to the same region on the sample surface plural times, a step of detecting each scattered light from the same region individually, and a step of adding or averaging the detected plural signals. The defect determination is performed based on the added or the averaged signal. The detection sensitivity may be improved while suppressing the temperature rise on the sample surface.

(2) In the step of irradiating the laser beam to the same region on the sample surface plural times of the surface defect inspection, the line illumination of the laser beam on the sample surface is performed, and the line illumination region is moved in the longitudinal direction at the pitch shorter than the length of the line illumination region in the longitudinal direction. As a result, the irradiation to the same region is performed plural times. This makes it possible to perform irradiation and detection to the same region plural times while maintaining the good throughput, thus improving the detection sensitivity.

(3) A surface defect inspection apparatus includes a stage which holds the sample, an illumination optical system for linearly irradiating the laser beam to the illumination region on the sample surface, and a detection optical system for detecting the scattered light from the line illumination region on the sample surface. The stage is moved in the longitudinal direction of the line illumination region on the sample surface at the feed pitch shorter than the longitudinal length of the line illumination region.

(4) The surface defect inspection apparatus for inspecting the sample includes a stage which holds the sample, an illumination optical system for irradiating the plural divided laser beams in array to the sample surface, and a detection optical system for detecting the scattered light from the plural illumination regions on the sample surface. The stage moves in the longitudinal direction of the line illumination region on the sample surface at the feed pitch shorter than the longitudinal length of the line illumination region.

These and other objects, features and advantages of the invention will be apparent from the following more particular description of preferred embodiments of the invention, as illustrated in the accompanying drawings.

DESCRIPTION OF THE PREFERRED EMBODIMENTS

Figure 1:
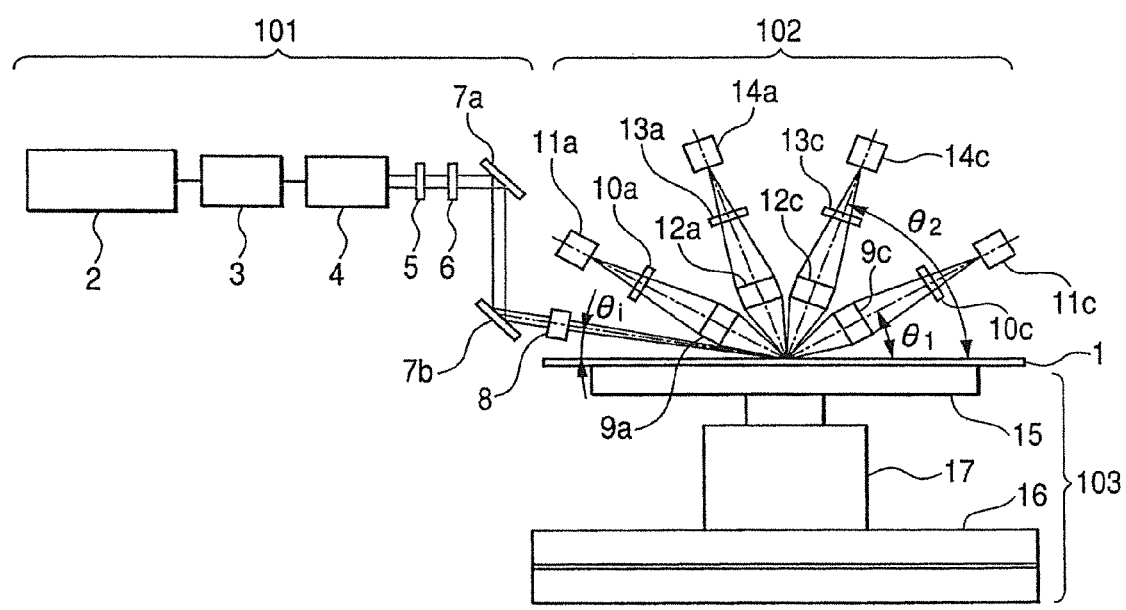
FIG. 1 is a view showing an embodiment (side view) of the present invention.
Figure 2:
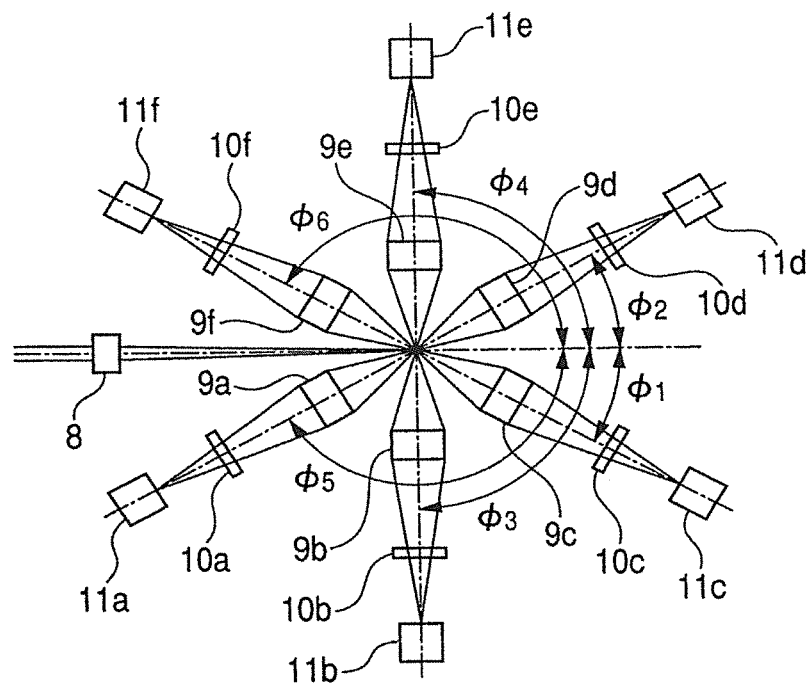
FIG. 2 is a view showing an embodiment (plan view) of the present invention.
Figure 3:
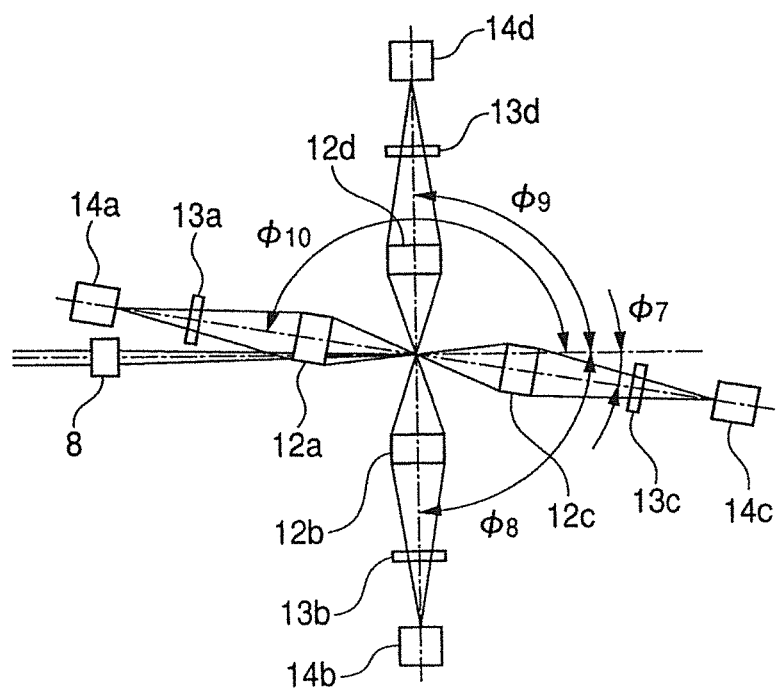
FIG. 3 is a view showing an embodiment (plan view) of the present invention.

An embodiment of the present invention will be described. FIGS. 1 to 3 show an example of an apparatus for detecting the defect/foreign matter on the semiconductor wafer before forming the circuit pattern. FIG. 1 is a side view, FIG. 2 is a plan view of a low angle detection system, and FIG. 3 is a plan view of a high angle detection system. The apparatus shown in FIG. 1 includes an illumination optical system 101, a detection optical system 102 and a wafer stage 103. The illumination optical system 101 includes a laser light source 2, an attenuator 3, a beam expander 4, wavelength plates 5, 6, and a condensing lens 8.

The laser beam from the laser light source 2 has its light intensity adjusted to the required value by the attenuator 3. The beam radius of the laser is expanded by the beam expander 4, and the polarization direction of the illumination is set by the wavelength plates 5, 6. The condensing lens 8 performs condensing and illumination to the detection area on a wafer 1. Mirrors 7a, 7b are employed for changing the illumination optical path when required. The wavelength plates 5 and 6 are employed to set the polarization of the illumination to S polarization, P polarization and circular polarization. Preferably the illumination elevation angle θi ranges from 5° to 25°.

The attenuator 3 includes a half-wave plate and a polarization beam splitter. The polarized angle of the beam from the laser light source (linear polarization) is inclined by the half-wave plate to change the intensity of light passing through the PBS (Polarized Beam Splitter). As the half-wave plate rotates, the polarized axis is changed to adjust the light intensity.

The detection optical system 102 includes a low angle detection system and a high angle detection system formed of scattered light detection lenses 9a, 9c, 12a, 12c, analyzers 10a, 10c, 13a, 13c, and photoelectric conversion elements 11a, 11c, 14a, 14c, respectively such that the scattered light from the foreign matter/defect on the detection area is substantially condensed on the light receiving surfaces of the photoelectric conversion elements 11, 14 by the scattered light detection lenses 9, 12. Each of the photoelectric conversion elements 11, 14 generates an electric signal in proportion to the received scattered light intensity so as to be processed in the signal processing circuit (not shown). As a result, the foreign matter/defect is detected to obtain such information as the size and location.

The photoelectric conversion elements 11, 14, for example, the TV camera, the CCD linear sensor, the TDI sensor and the photomultiplier tube, receive the scattered light condensed by the detection optical system 102 so as to be photoelectrically converted. The analyzers 10, 13 are employed for detecting only the component in the specific direction contained in the scattered light. Preferably, the detection elevation angle (center angle) $\theta_1$ of the low angle detection system is set to the value ranging from 15° to 35°, and the detection elevation angle (center angle) $\theta_2$ of the high-angle detection system is set to the value ranging from 45° to 70°

The wafer stage 103 includes a chuck 15 for holding the wafer 1, a rotating mechanism 17 for rotating the wafer 1, and a direct feed mechanism 16 for directly feeding the wafer 1 in the radial direction. The wafer 1 is subjected to the rotation scanning and the direct feed movement in the horizontal direction by the wafer stage 103 to allow the detection of the foreign matter/defect in the entire region of the wafer 1 and classification of the defect.

FIG. 2 is a plan view of the low angle detection system, which allows the multi-directional detection. In FIG. 2, 9a-9f denote scattered light detection lenses, 10a-10f denote analyzers, 11a-11f denote photoelectric conversion elements. The embodiment allows the 6-direction detection. Each output of the respective photoelectric conversion elements 11 is subjected to such calculation as addition, subtraction, and division in accordance with the usage. Preferably each detection azimuth (center angle) is set to 20° to 50° ($\phi_1$), −20° to −50° ($\phi_2$), 70° to 110° ($\phi_3$), −70° to 110° ($\phi_4$), 130° to 160° ($\phi_5$), and −130° to −160° ($\phi_6$) with respect to the illumination direction, respectively.

FIG. 3 is a plan view of the high angle detection system similar to the one shown in FIG. 2, which allows the multi-directional detection. In FIG. 3, 12a-12d denote scattered light detection lenses, 13a-13d denote analyzers, 14a-14d denote photoelectric conversion elements. The embodiment allows the 4-direction detection. Each output of the respective photoelectric conversion elements 14 is subjected to such calculation as addition, subtraction, and division in accordance with the usage. Preferably each detection azimuth (center angle) is set to ±10° ($\phi_7$), 80° to 110°($\phi_8$), −80° to −110° ($\phi_9$), and 180°±10° ($\phi_{10}$) with respect to the illumination direction, respectively.

Figure 4:
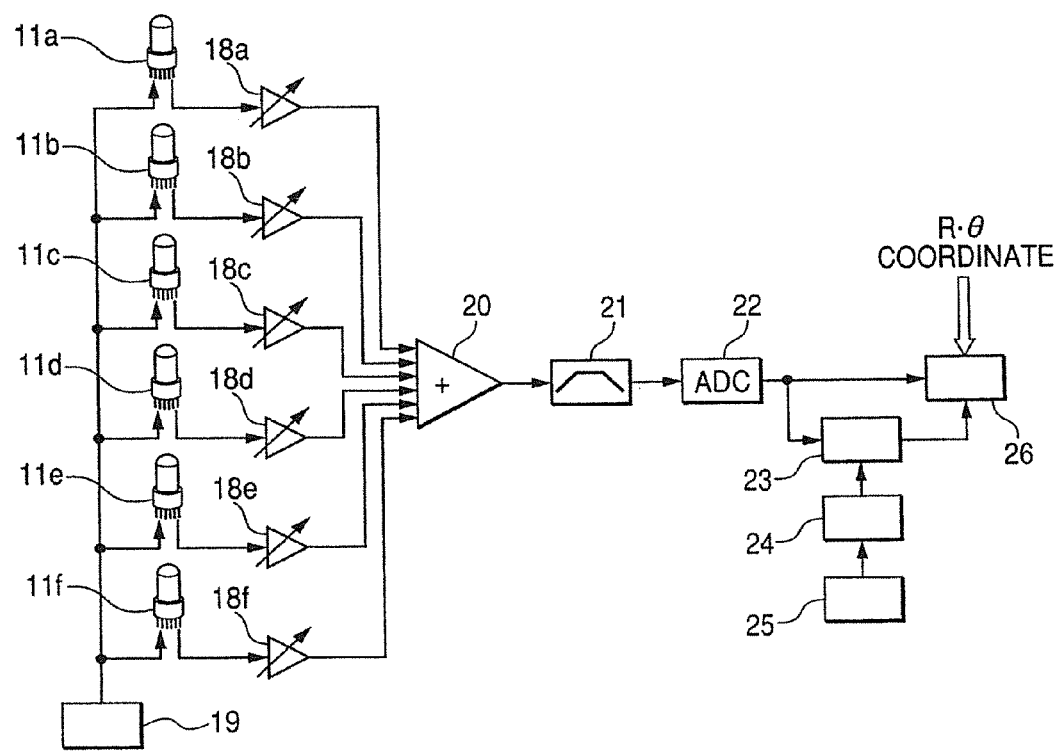
FIG. 4 is an explanatory view of a signal processing circuit.

FIG. 4 shows an example of the signal processing performed in the low angle detection system which employs the photomultiplier tube as the photoelectric conversion element 11. The photomultiplier tube 11a-11f requires application of the high voltage supplied from a high voltage DC power source 19. The output of the photomultiplier tube 11 is subjected to the current-voltage conversion and the required voltage amplification by the amplifier circuit 18a-f, which is then added by an adder circuit 20. At this time, the amplifier circuit 18 adjusts the amplification factor for correcting the difference in sensitivity of the photomultiplier tube 11.

Figure 5:
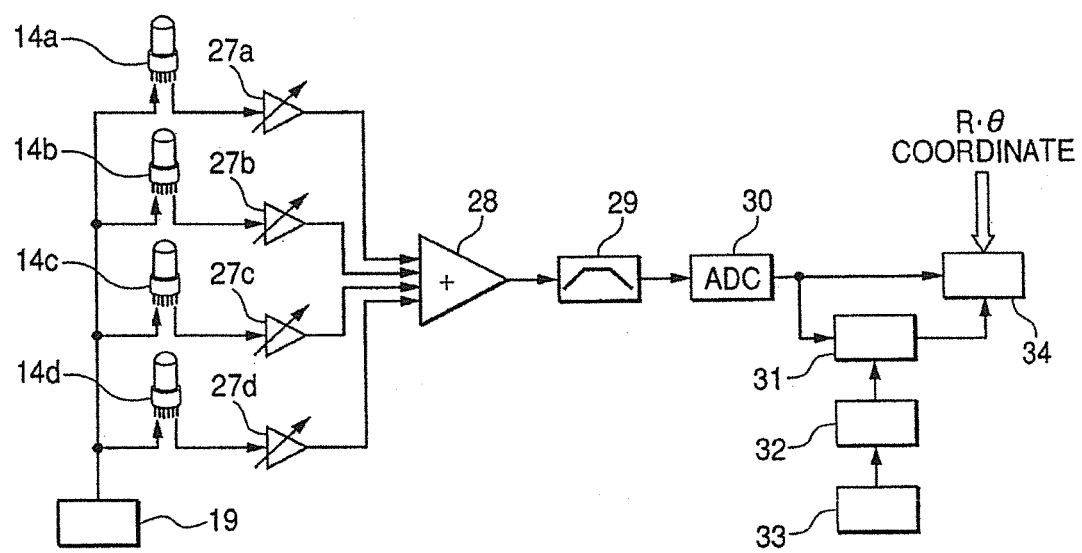
FIG. 5 is an explanatory view of a signal processing circuit.

The output of the adder circuit 20 has the DC component and the unnecessary noise eliminated by the band-pass filter 21 so as to be subjected to the digital conversion by an AD conversion circuit 22. The output of the AD conversion circuit 22 is compared with a threshold value by a comparison circuit 23. When the output exceeds the threshold value, the AD conversion value and the R·θ coordinate are loaded in a defect memory 26. The threshold value is set to a latch 24 from the CPU (not shown) via an interface 25. The content of the defect memory 26 is read from the CPU (not shown) so as to be used for displaying the defect map and classifying the defect. FIG. 5 shows an example of the signal processing in the high angle detection system, the content of which is the same as the one shown in FIG. 4.

In FIG. 5, 14a-14d denote photoelectric conversion elements, 27a-27d denote the amplifier circuits, 28 denotes an adder circuit, 29 denotes the band-pass filter, 30 denotes an AD conversion circuit, 31 denotes a comparison circuit, 32 denotes a latch, 33 denotes an interface, 34 denotes the defect memory.

Figure 6:
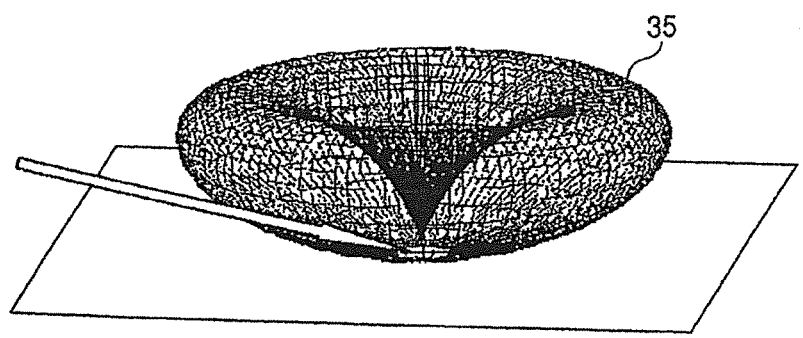
FIG. 6 is a view representing the intensity distribution of the scattered light from the tiny defect.

FIG. 6 shows an example of a scattered light intensity distribution 35 which is caused by the tiny defect upon illumination with the P polarization. When the dimension of the defect is approximately ⅕ of the illumination wavelength or shorter, the scattered light intensity distribution becomes isotropic as shown in FIG. 6. In this case, the respective detection signals become substantially the same value (S). A shot noise (N) occurs upon the photoelectric conversion in the photomultiplier tube 11.

The shot noise (N) output from each photomultiplier tube 11 is random, and the SN ratio of the output signal from the photomultiplier tube 11 becomes S/N. Referring to FIGS. 4 and 5, when all the detection signals are added and averaged, the shot noise is averaged to become $1/\sqrt{6}$. Then the S/N ratio of the detection signal is increased by $\sqrt{6}$ times. Each individual processing for the photomultiplier tube 11 makes it possible to detect the tiny defect. When the addition/averaging is performed in the case where the scattered light intensity distribution is biased like scratch to be detected only in the single photomultiplier tube 11, the detection signal becomes 1/6, and the shot noise becomes $1/\sqrt{6}$, thus reducing the S/N ratio to $1/\sqrt{6}$ compared with the process for each of the photomultiplier tube 11 individually.

Figure 7:
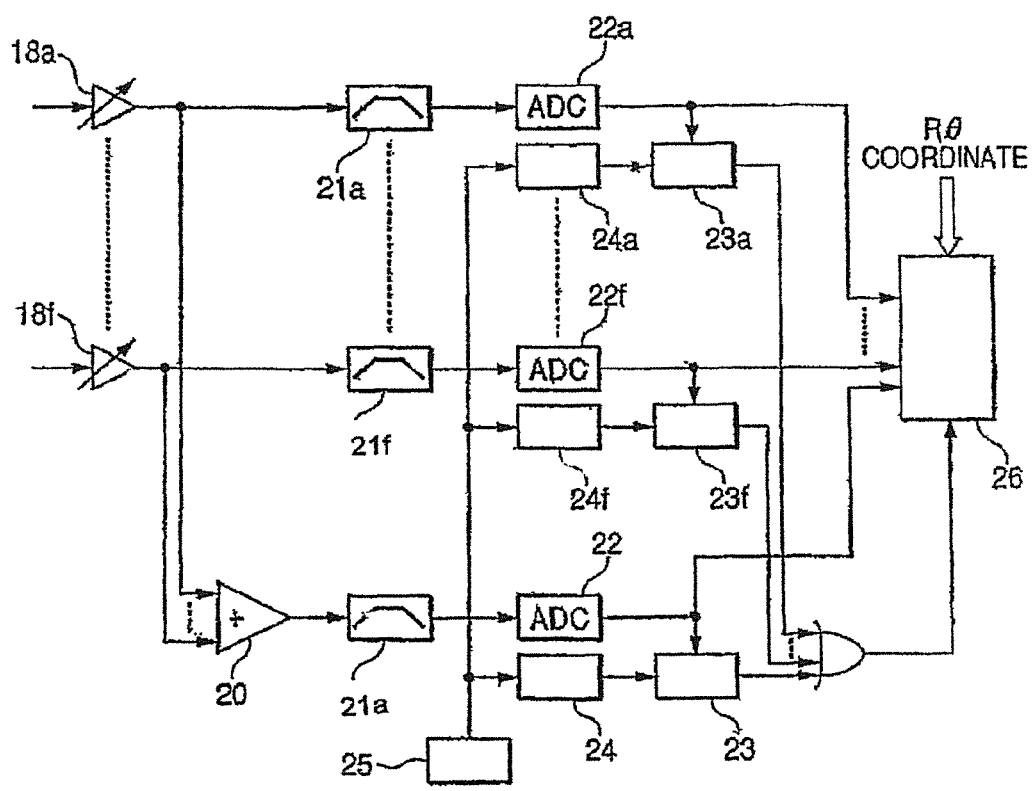
FIG. 7 is an explanatory view of a signal processing circuit.

In order to avoid the aforementioned disadvantage, a first embodiment is provided as shown in FIG. 7. The circuit which is the same as the processing circuit shown in FIG. 4 is added for each of the photomultiplier tubes 11a-11f. In FIG. 7, 18a-18f denote the amplifier circuits, 21a-21f denote the band-pass filter, 22a-22f denote an AD conversion circuit, 24a-24f denote latches. The output of the comparison circuit 23a-23f are subjected to the logic OR operation. When any one of the value exceeds the threshold value, the outputs of the all the AD conversion circuits 22 and the R·θ coordinate are loaded in the defect memory 26. This makes it possible to prevent the error failing to detect the anisotropic defect with the directionality in the scattered light intensity distribution.

Figure 8:
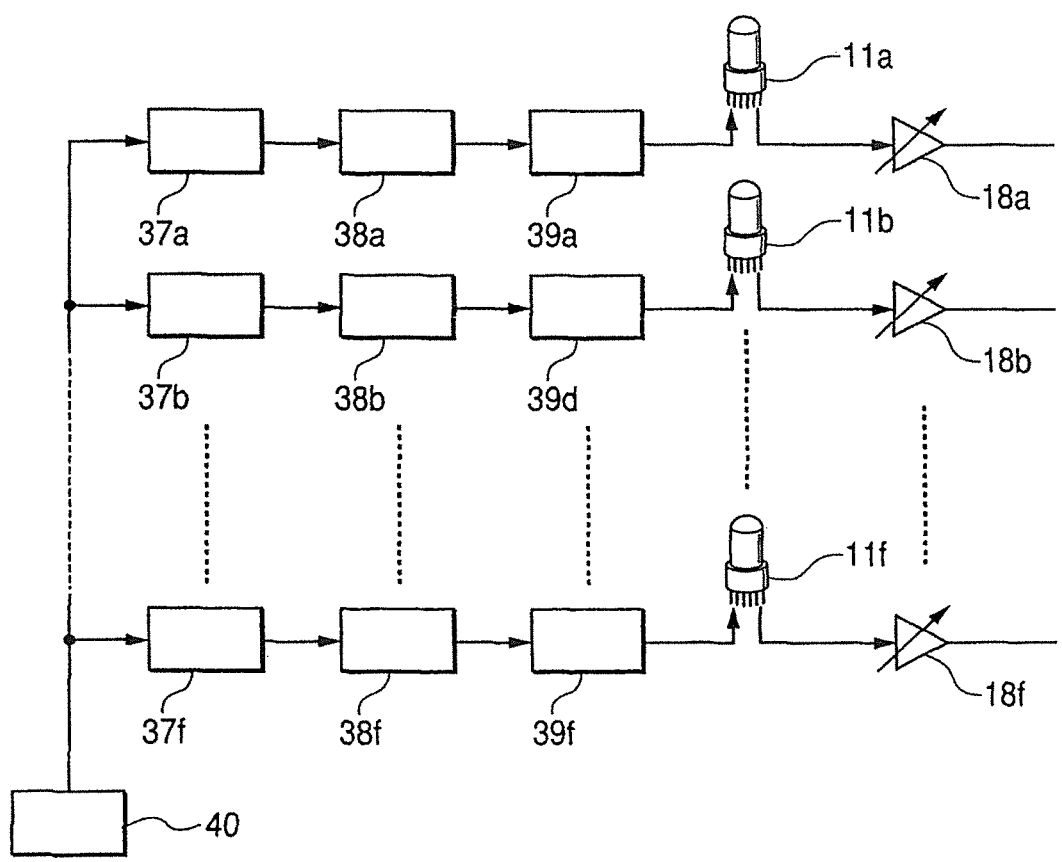
FIG. 8 is an explanatory view of the process for adjusting the sensitivity of the photomultiplier tube.

FIG. 8 shows an embodiment for correcting the difference in sensitivity of the photomultiplier tube 11a-11f. A power unit 39a-39f are structured to adjust the high application voltage in accordance with the input voltage. The power unit of the type of C4900 produced by Hamamatsu Photonics may be employed as one of the exemplary power units. The voltage value is written into the latch 37a-37f via the interface 40 to convert the value into the voltage value by the DA conversion circuit 38a-38f so as to be applied to the power unit 39a-39f. This makes it possible to supply the high application voltage to the photomultiplier tube 11. The change in the voltage value written into the latch 37a-37f allows the sensitivity of the photomultiplier tube 11 to be adjusted from the CPU. The adjustment of the amplification factor by the amplification circuit 18a-18f may be performed together with the aforementioned operation to allow the easy correction of the difference in the sensitivity.

The intensity and distribution of the scattered light on the wafer surface varies depending on the space frequency/degree of the roughness thereon. When the scattered light intensity on the wafer surface detected by the photomultiplier tube 11a-aaf are set to Su, the shot noise generated thereby becomes $\sqrt{Su}$. In the case where the scattered light intensity on the wafer surface detected by the photomultiplier tube 11a-11f vary depending on each of the photomultiplier tubes 11a-11f, the resultant shot noise will vary. It is necessary to change the threshold value for detecting the defect. An embodiment to cope with the aforementioned problem and the detailed process will be described referring to FIGS. 9 and 10, respectively.

Figure 9:
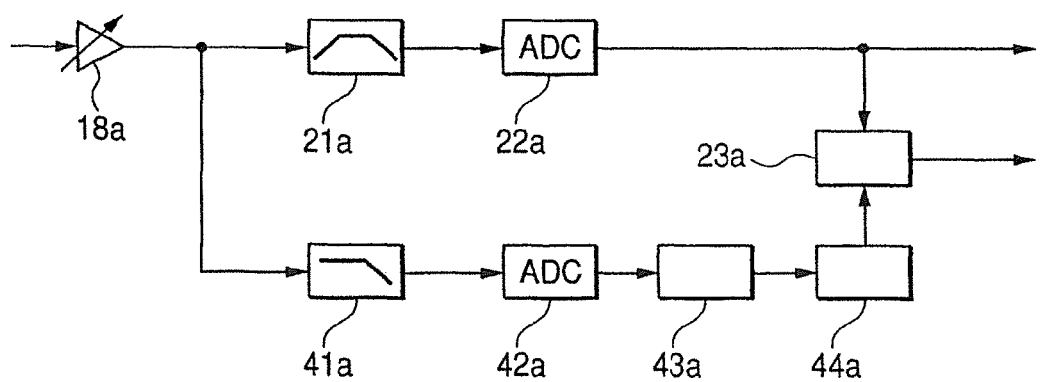
FIG. 9 is an explanatory view of the process for setting the threshold value.
Figure 10:
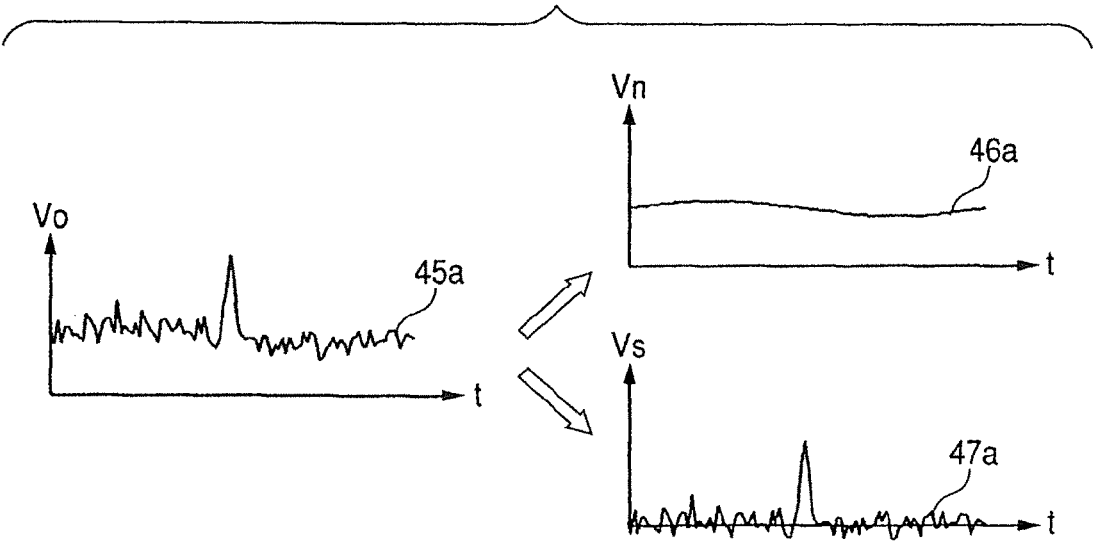
FIG. 10 is an explanatory view with respect to the process shown in FIG. 9.

In FIGS. 9 and 10, an output signal 45a from the amplifier circuit 18a is separated into a wafer signal 46a and a defect signal 47a which contains the shot noise using the band-pass filter 21a and the lowpass filter 41a. The wafer signal 46a which has passed through the lowpass filter 41a is used for setting the threshold value. The signal derived from the wafer signal 46a is subjected to the digital signal conversion by the AD conversion circuit 42a, and is formed into the threshold value Vth by the calculation circuit 43a so as to be set in the latch 44a. The shot noise 47a is subject to the digital conversion by the AD con version circuit 22a, and is sent to a comparison circuit 23a. The wafer signal also is sent to the comparison circuit 23a. The shot noise is proportional to the square root of the wafer signal Su, and the threshold value Vth is calculated through the following equation (1):

$$Vth = k \cdot \sqrt{(Su \cdot \Delta f)}$$

where k denotes the constant and $\Delta f$ denotes a frequency band of the circuit. In FIG. 10, left side graph shows the out put signal 45a, in which y-axis Vo denotes output signal, and x-axis denotes time (t). Upper right side graph shows the wafer signal 46a, in which y-axis Vn denotes wafer signal, and x-axis denotes time (t). Lower right side graph shows the defect signal 47a, in which y-axis Vs denotes defect signal, x-axis denotes time (t).

Figure 11:
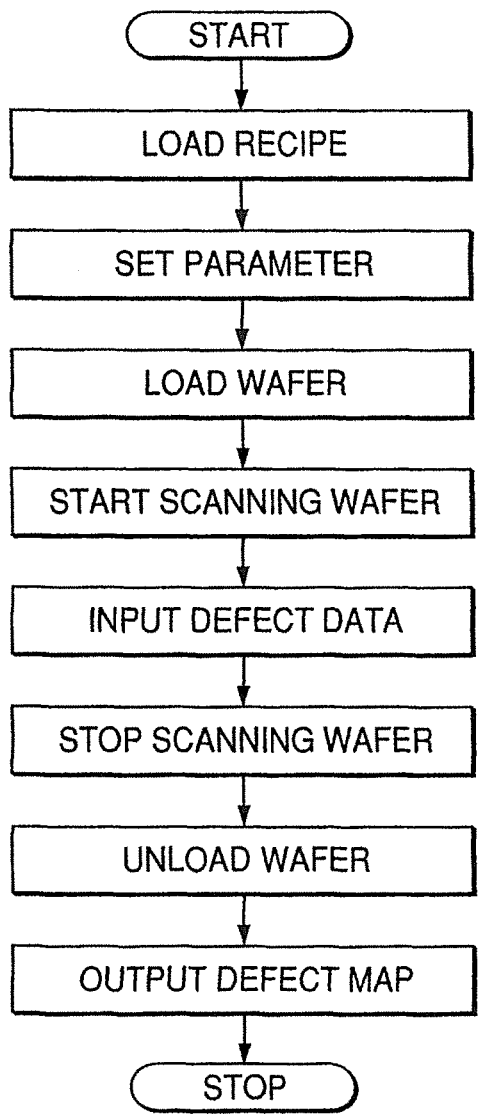
FIG. 11 is an explanatory view of the inspection flow.

FIG. 11 shows an example of the inspection routine. The inspection recipe is loaded to set the required parameter in the apparatus. The wafer is loaded and inspected to input the defect data from the defect memory. When the inspection ends, the wafer scan (rotation and the single axis feed) is stopped so as to unload the wafer. Thereafter, the defect map is displayed on the GUI screen as required.

Figure 12:
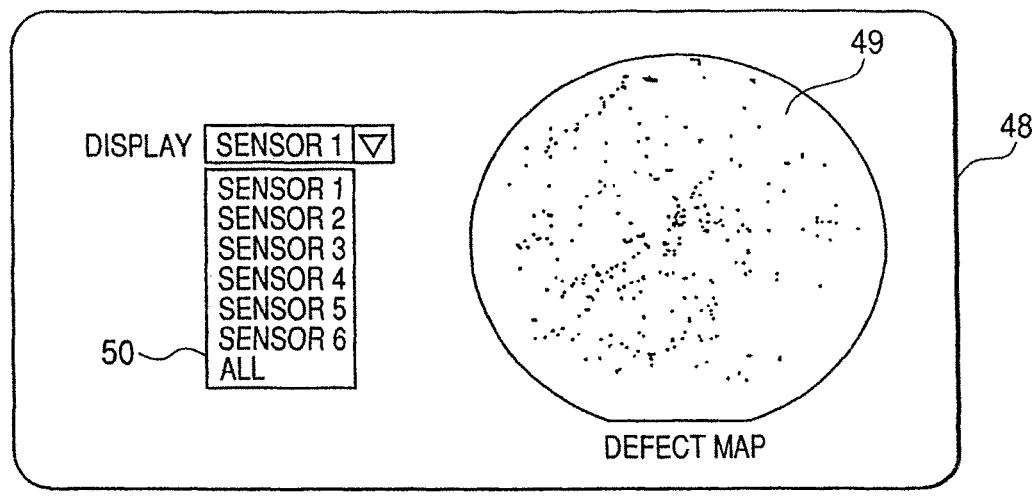
FIG. 12 is an explanatory view showing an example of GUI.

FIG. 12 shows an example of the GUI. A GUI screen 48 includes at least a defect map 49 displayed after the end of the inspection, and a defect map display sensor selector screen 50.

Figure 13:
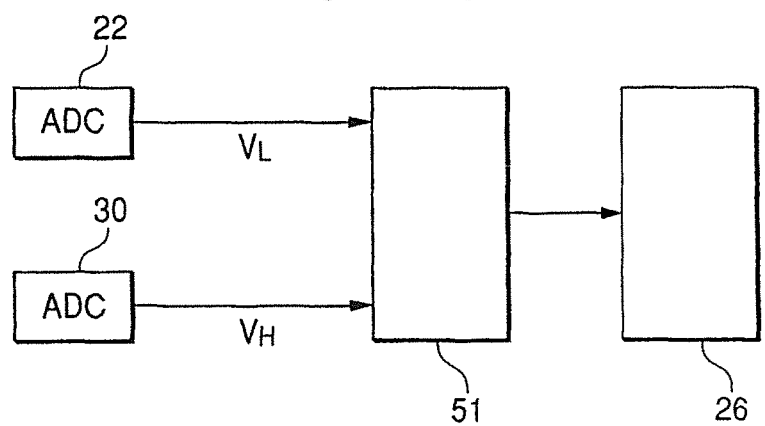
FIG. 13 is an explanatory view of the defect classification processing circuit.

FIG. 13 shows an example of distinguishing the defect. The detection signal $V_L$ of the low angle detection system flows from Ad conversion circuit 22, and the detection signal $V_H$ of the high angle detection system flows from Ad conversion circuit 30. The ratio of the detection signal $V_L$ of the low angle detection system to the detection signal $V_H$ of the high angle detection system is calculated by a processing circuit 51, and the calculation result is written into the defect memory. The detailed process will be described referring to FIG. 14. The calculation results are plotted on the graph having an x-axis as $V_L$ and the y-axis as $V_H$. On the graph, the concave defect (COP, scratch and the like) is observed in an area 53 above the threshold curve 52, and the convex defect is observed in an area 54 below the threshold curve 52. The threshold curve 52 is set to allow the appropriate distinguishing between the concave defect and the convex defect (defect type).

Figure 14:
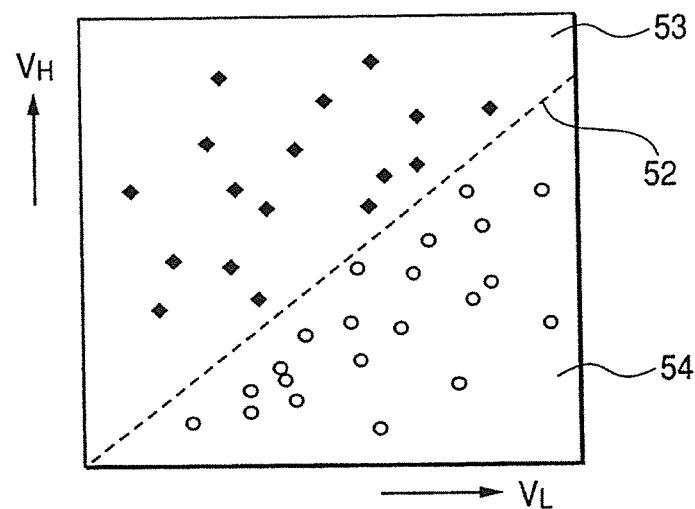
FIG. 14 is an explanatory view of the defect classification.

Referring to FIG. 14, each of the defects in the area below the dotted line 52 is the convex defect, and each of the defects in the area above the dotted line 52 is the concave defect. In most of the cases, the concave defect has been existed in the Si wafer, and the convex defect is likely to be caused in the apparatus. The number of the convex defects larger than that of the concave defects in spite of the same defect density tends to indicate the problem in the manufacturing apparatus.

The above explanation has been made when the photomultiplier tube 11 is used as the photoelectric conversion element. However, the relationship between the shot noise and the defect detection signal is kept unchanged when the CCD is used as the photoelectric conversion element. Accordingly, the aforementioned description is applicable to the case where the element other than the photomultiplier tube 11 is used as the photoelectric conversion element.

The detection signals of the multi-directionally detected scattered lights are added to detect the tiny defect, and to prevent the error failing to detect the anisotropic defect by performing the individual process for each of the detection signals.

The obtained defect data are automatically analyzed to make a determination whether the defect has been caused by the problem of the apparatus, or it has already existed on the substrate.

Figure 15:
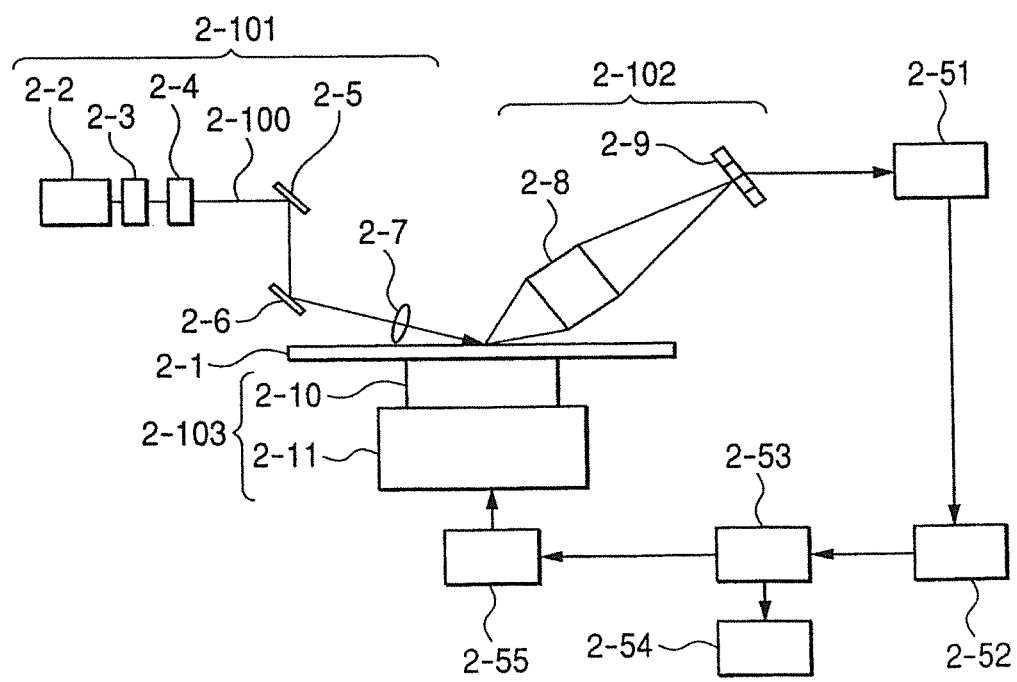
FIG. 15 is a view schematically showing the structure of the inspection apparatus according to the present invention.

An example of the embodiment according to the invention for solving the aforementioned problem will be described referring to FIG. 15. FIG. 15 schematically shows the structure including an illumination optical system 2-101, a detection optical system 2-102, a wafer stage 2-103, and a circuit/signal processor. The illumination optical system 2-101 includes a laser light source 2-2, a beam expander 2-3, a homogenizer 2-4, mirrors 2-5, 2-6, and a cylindrical lens 2-7. A laser beam 2-100 irradiated from the laser light source 2-2 allows the beam radius to be adjusted to the required size by the beam expander 2-3, and converted by the homogenizer 2-4 into the uniform illumination distribution. It is further subjected to the line illumination in the inspected region on the wafer 2-1 by the cylindrical lens 2-7.

The laser light source for generating ultraviolet or extra ultraviolet laser beams may be employed as the laser light source 2.

The homogenizer 2-4 is used for making the illumination intensity uniform. However, the diffraction optical element and the fly eye lens may be used to make the illumination intensity uniform. The illumination may be performed without using the homogenizer 2-4. The illumination without using the homogenizer suppresses the attenuation of the laser beam intensity, thus allowing the illumination with the high intensity.

The cylindrical lens 2-7 is used for the line illumination. However, the anamorphic optical system formed of plural prisms may be used to change the beam radius on the plane perpendicular to the optical axis with respect to only one direction such that the condensing lens is used for the line illumination to the sample. The use of the anamorphic optical system is effective in view of easy adjustment of the optical axis.

Figure 16:
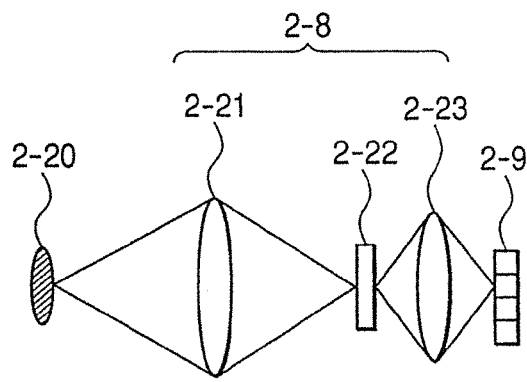
FIG. 16 is an explanatory view which shows the imaging system in detail.

The detection optical system 2-102 includes an imaging system 2-8 and a photodiode array 2-9. FIG. 16 illustrates the detection optical system 2-102 in detail. The detection optical system 2-102 includes a condensing lens 2-21, an image intensifier 2-22, an imaging lens 2-23 and a photodiode array 2-9. The light scattered from the beam spot 2-20 is condensed by the condensing lens 2-21. The scattered light is amplified by the image intensifier 2-22 so as to be imaged on the photodiode array 2-9 through the imaging lens 2-23.

The image intensifier 2-22 is used for amplifying the weak scattered light to be detectable. However, instead of the image intensifier, the sensor with high gain, for example, EM-CCD, the multi-anode PMT and the like may be employed. The use of the aforementioned sensor is effective in view of downsizing the apparatus.

The photodiode array 2-9 is used for receiving the scattered light to be photoelectrically converted. However, TV camera, CCD linear sensor, TDI, photodiode array, multi-anode PMT, and the like may be employed. For example, the use of the 2D sensor allows the wide region to be inspected at one time.

The photodiode array 2-9 generates the electric signal corresponding to the received light intensity so as to be subjected to the required process by the analog circuit 2-51 including amplification, noise process, and analog-digital conversion. The signal processor 2-52 adds plural optical signals scattered from substantially the same region and performs the defect determination to display the defect map by the map output section 2-54 via a CPU 2-53.

The wafer stage 2-103 is formed of a chuck (not shown) for holding the wafer 2-1, a rotating stage 2-10 for rotating the wafer, and a parallel stage 2-11 for moving the wafer in the radial direction. The wafer stage 2-103 performs the rotation scan and the parallel scan to spirally illuminate the entire sample surface. The stage control section 2-55 controls the rotating speed and the parallel advancing speed so as to illuminate the desired region.

As a feature of the present invention, the line illumination is performed to the sample surface, and the sample is moved in substantially the same direction as the longitudinal direction of illumination while being rotated. As a result, the entire sample surface may be spirally illuminated to allow the surface defect inspection based on the detected scattered light.

FIG. 15 shows the example where the single illumination optical system and the single detection optical system are employed. However, plural illumination optical systems and detection optical systems may be employed likewise the case shown in FIG. 17 including an oblique illumination optical system 2-101a for illuminating the sample from the low elevation angle, a perpendicular illumination optical system 2-101b for illuminating the sample from substantially the perpendicular direction, a low angle detection optical system 2-102a for detecting the sample at the low elevation angle, and a high angle detection optical system 2-102b for detecting the ample at the higher elevation angle compared with the low angle detection optical system.

The oblique illumination optical system 2-101*a* includes the laser light source 2-2, the beam expander 2-3, the homogenizer 2-4, the mirrors 2-5, 2-6*a*, and a cylindrical lens 2-7*a*. Likewise, the perpendicular illumination optical system 2-101*b* includes the laser light source 2-2, the beam expander 2-3, the homogenizer 2-4, a mirror 2-6*b*, and a cylindrical lens 2-7*b*. The aforementioned structures allow any of the components of the embodiment shown in FIG. 15 to be omitted and replaced.

In this case, the mirror 2-5 is structured to change the advancing direction of the laser beam 2-100, and the optical system is switchable between the oblique illumination optical system 2-101*a* and the perpendicular illumination optical system 2-102*b* in need.

The oblique illumination optical system may be selected to improve the detection sensitivity, and the perpendicular illumination optical system is selected to improve the capability of classifying the defect. Accordingly, the desired system may be selected depending on the usage.

The low angle detection optical system 2-102*a* includes an imaging system 2-8*a* and a photodiode array 2-9*a*. Likewise, the high angle detection optical system 2-102*b* includes an imaging system 2-8*b* and a photodiode array 2-9*b*. The imaging system 2-8*a* includes the condensing lens, the image intensifier, and the imaging lens (not shown). The imaging system 2-8*b* has the same structure. The aforementioned structures allow any of the components of the embodiment shown in FIG. 15 to be omitted and replaced.

Each of the photodiode arrays 2-9*a* and 2-9*b* generates the electric signal corresponding to the received light intensity so as to be subjected to the required process by the analog circuits 2-51*a* and 2-51*b* including amplification, noise process, and analog-digital conversion. Then the signal processor 2-52 adds the plural optical signals scattered from substantially the same region, and performs the defect determination such that the defect map is displayed by the map output section 2-54 via the CPU 2-53.

In the embodiment, substantially the same location is detected at the different elevation angle at substantially the same time. Any of the optical system selected from the low angle detection optical system and the high angle detection optical system may be used for the inspection by adjusting the sensitivity of the respective sensors such that the dynamic range of the detected particle size is widened.

The use of the combination of the illumination optical system and the detection optical system makes it possible to improve the accuracy in the defect classification. For example, as for the convex defect, the low angle detection optical system is capable of detecting the large scattered light upon the oblique illumination. As for the concave defect, the high angle detection optical system is capable of detecting the large scattered light upon the perpendicular illumination.

Figure 17:
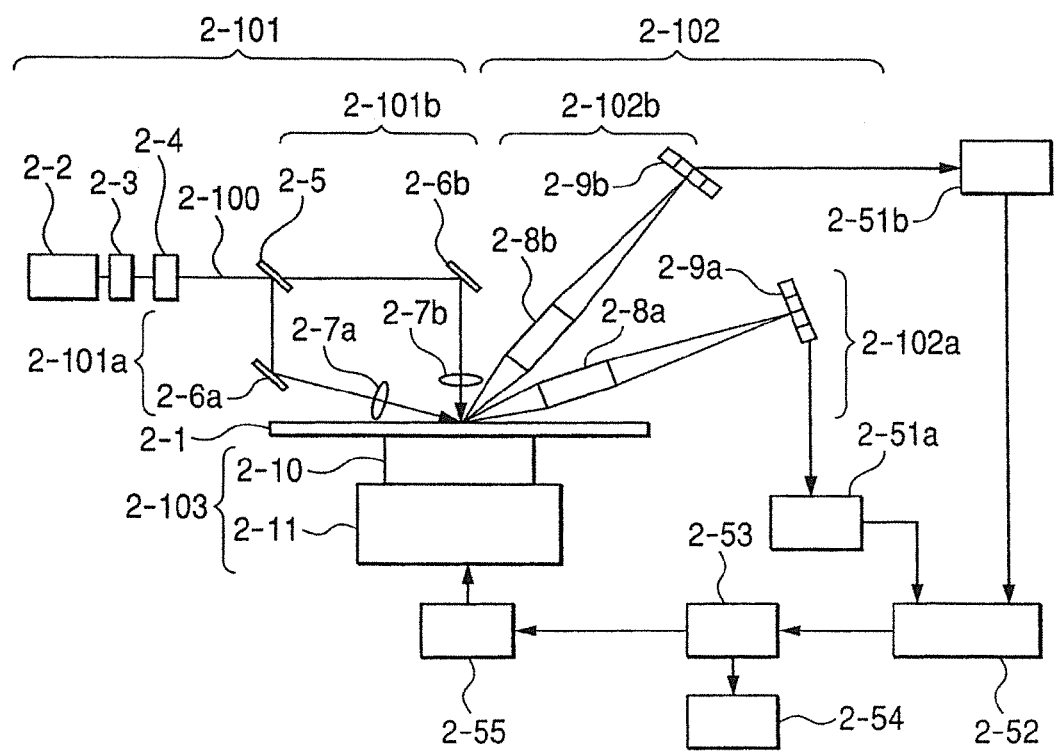
FIG. 17 is a view schematically showing the illumination optical system and the detection optical system which exist at different elevation angles.
Figure 18:
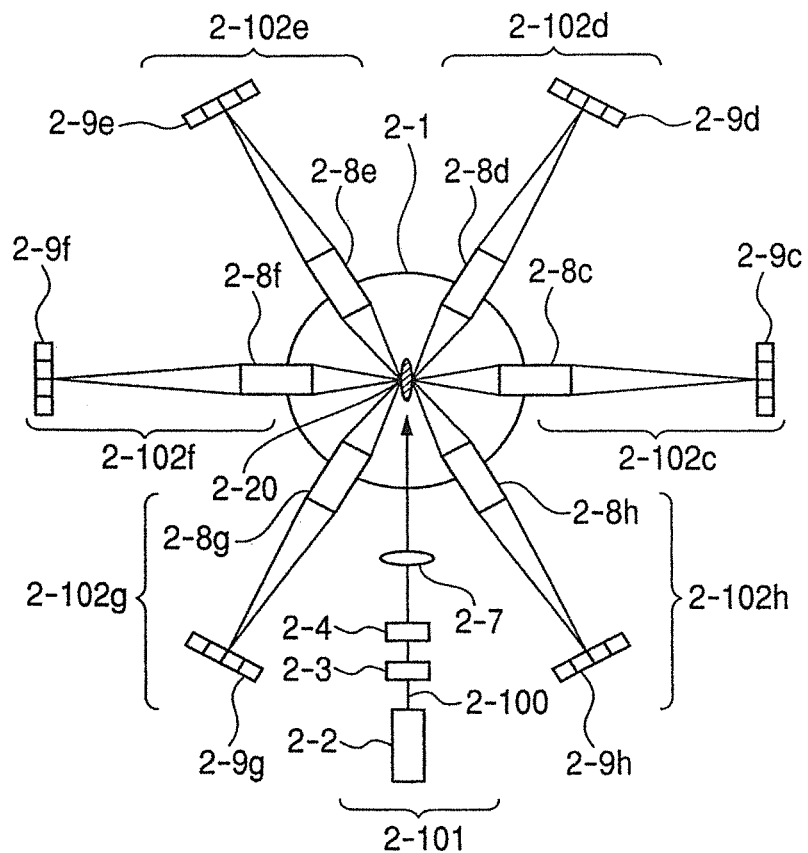
FIG. 18 is a view schematically showing the detection optical systems each in the different azimuth direction.

Referring to FIG. 17, the example where the detection optical systems exist in the different elevation angle directions. However, plural detection optical systems may be provided in the different azimuth directions as shown in FIG. 18. FIG. 18 is a view of the embodiment according to the present invention when seen from above, which shows a wafer 2-1, the illumination optical system 2-101, and detection optical systems 2-102*c* to 2-102*h*. The detection optical systems 2-102*c* to 2-102*h* are formed of the corresponding imaging systems 2-8*c* to 2-8*h*, and the respective photodiode arrays 2-9*c* to 2-9*h*. The detection signal is subjected to the required process by the analog circuit including amplification, noise processing and analog-digital conversion. The signal processor adds the plural optical signals scattered from substantially the same region and performs the defect determination. Then the defect map (not shown) is displayed by the map output section via the CPU. With respect to the structure of the detection optical system, each of the imaging systems 2-8*c* to 2-8*h* is formed of the condensing lens, the image intensifier, and the imaging lens (not shown), respectively.

The use of the detection optical system which exists at plural azimuths allows the detection optical system capable of detecting more scattered lights from the defect while suppressing the noise to be selected by performing the inspection when the angular property of the scattered light caused by the size/configuration of the defect, film type of the sample, and surface roughness. This makes it possible to improve the detection sensitivity.

Referring to FIG. 18, six detection optical systems are arranged in different azimuth directions. However, the number of the detection optical systems does not have to be limited to six, but may be arbitrarily set to be arranged in the arbitral azimuth direction. The plural detection optical systems do not have to be arranged at substantially the same elevation angle. Furthermore, the detector does not have to be arranged in substantially the same azimuth direction.

In the present invention, the line illumination and the scanning allow the illumination to the same defect plural times. The generally employed inspection method will be described first, and then the inspection method according to the present invention will be described hereinafter.

The stage advances in parallel at substantially the constant speed in the radial direction (R direction) while rotating. It is assumed that the advancing distance in the radial direction in the cycle of the single rotation is referred to as the feed pitch. The rotation/parallel advancement allows the spiral scan on the entire sample surface. However, the length of the beam spot in the radial direction is substantially the same as the feed pitch length. In most of the case, the illumination to the single defect is performed only once.

In the present invention, the line illumination is performed, and the beam spot length is made longer than the pitch length to illuminate the same defect plural times.

Figure 19:
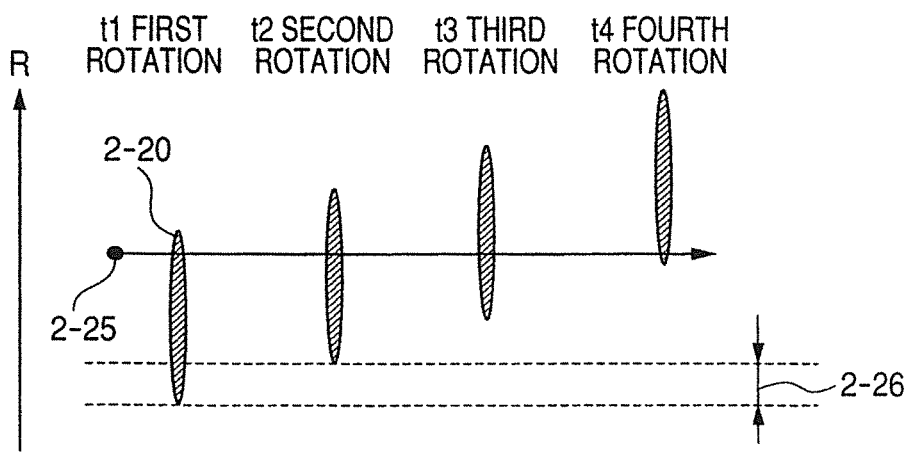
FIG. 19 is an explanatory view representing the inspection method for performing the illumination to the same defect plural times.

Referring to FIG. 19, the defect 2-25 is illuminated four times in the condition where the length of the beam spot 2-20 is four times longer than that of the feed pitch 2-26. The illumination performed plural times will be described referring to FIG. 19. At a time point t1, the first illumination is performed to the defect 2-25. At a time point t2, the wafer rotates at the single round. The beam spot advances in the radial direction by the distance substantially corresponding to the feed pitch 2-26 to illuminate the defect 2-25 again. Then at the time points t3 and t4, the wafer rotates at the single round, respectively to illuminate the defect 2-25. Referring to FIG. 19, the defect 2-25 may be illuminated four times, and the detected light is added by the analog circuit or the signal processor. The number of times for illumination is not limited to four, but may be arbitrarily set so long as it is plural times.

The improvement in the detection sensitivity by adding the plural scattered lights in the present invention will be described.

Figure 20:
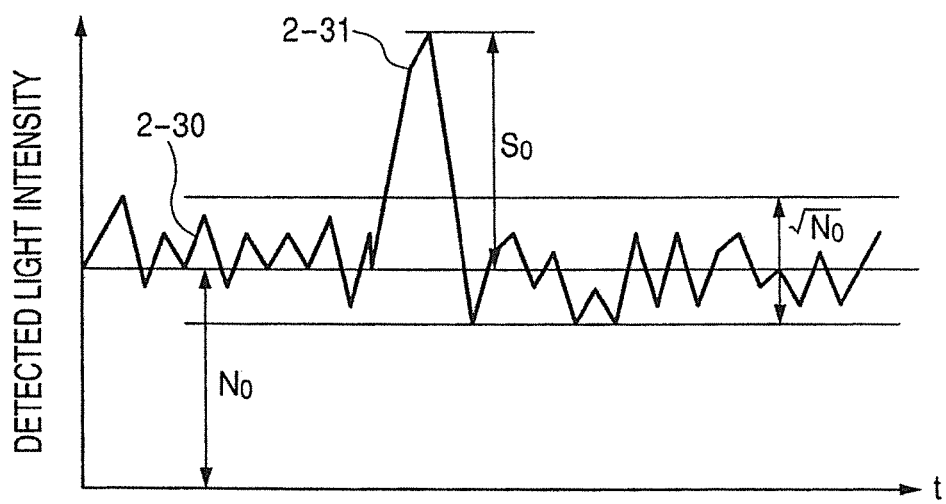
FIG. 20 is an explanatory view of the definition of SN ratio.

The improvement in the detection sensitivity will be described in reference to the SN ratio defined in FIG. 20. Referring to FIG. 20, the y-axis of the graph denotes the detected light intensity, and x-axis denotes the time (t). The sample surface is constantly illuminated even if no defect exists on the beam spot so as to continuously detect the scattered light 2-30 generated in accordance with each size of concavity and convexity of the wafer roughness. Assuming that the average intensity of the scattered lights from the wafer roughness is set to $N_0$, the detected light intensity fluctuates at the amplitude of $\sqrt{N_0}$ owing to fluctuation on the sensor light receiving surface caused by the photoelectric conversion, thus generating the noise. The defect which exists on the beam spot generates the scattered light 2-31. Assuming that the intensity of the scattered light from the defect is set to $S_0$ having the value $N_0$ as the standard, the SN ratio is defined as "$S_0/\sqrt{N_0}$".

The scattered light from the same defect is added n times to increase the scattered light intensity from the defect from $S_0$ to $n \times S_0$, and the scattered light intensity from the wafer roughness from $N_0$ to $n \times N_0$. That is, the SN ratio becomes "$n \times S_0/\sqrt{(n \times N_0)}$", and the detection sensitivity is intensified by $\sqrt{n}$ times.

It is effective to illuminate the same defect plural times by increasing the beam spot to be longer than the feed pitch, that is, generating the line illumination. Instead of increasing the beam spot length, the feed pitch length may be decreased to allow the same defect to be illuminated plural times. In this case, however, the throughput is reduced.

Figure 21:
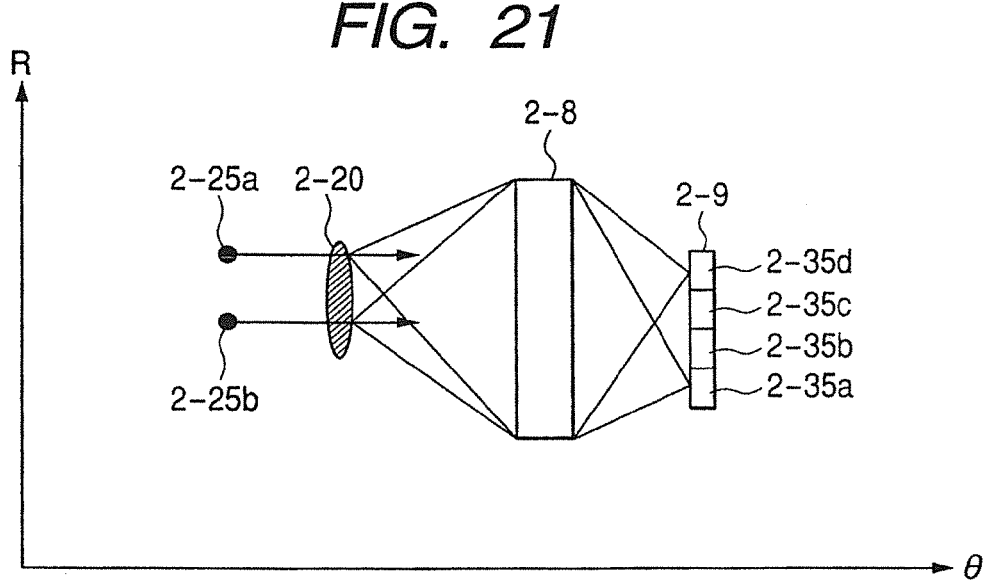
FIG. 21 is an explanatory view representing the detection of the scattered light from the defect in separated way using the photodiode array when plural defects exist on the beam spot.

Referring to FIG. 21, the photodiode array is used to divide the beam spot to be detected such that each scattered light from the two or more simultaneously illuminated defects may be detected individually. The photodiode array having four light receiving sections 2-35$a$, 2-35$b$, 2-35$c$, and 2-35$d$ will be described.

When the defects 2-25$a$ and 2-25$b$ are simultaneously illuminated on the beam spot 2-20, they may be divided by the imaging system 2-8 with respect to the light receiving sections 2-35$a$ and 2-35$d$ of the photodiode array 2-9. The divided beam spot is detected to allow the noise from the wafer roughness to be reduced, resulting in the effect expected to improve the detection sensitivity.

In the inspection method according to the present invention, the substantially the same region is illuminated with the line illumination plural times, and the plural scattered lights are added to improve the detection sensitivity. The detection sensitivity may be improved without decreasing the illumination wavelength to be short, or without using the process for increasing the laser output and reducing the beam spot. That is, the embodiment of the present invention is capable of improving the detection sensitivity while suppressing the damage to the sample.

In the illumination optical system, the laser beam intensity distribution generally has a Gaussian distribution. In the present invention, however, the illumination may be performed with the uniform intensity distribution.

Figure 22:
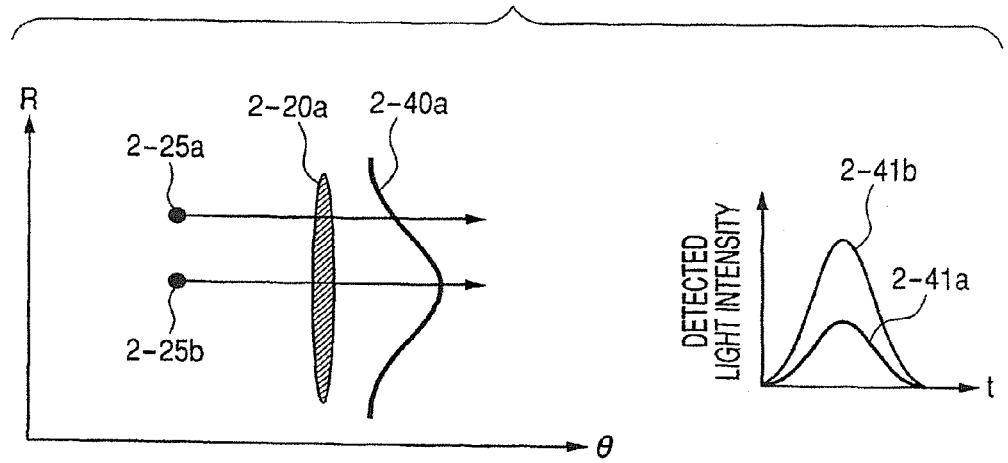
FIG. 22 is an explanatory view showing the relationship between the position through which the defect passes and the generated scattered light intensity when the illumination intensity distribution is Gaussian distribution.
Figure 23:
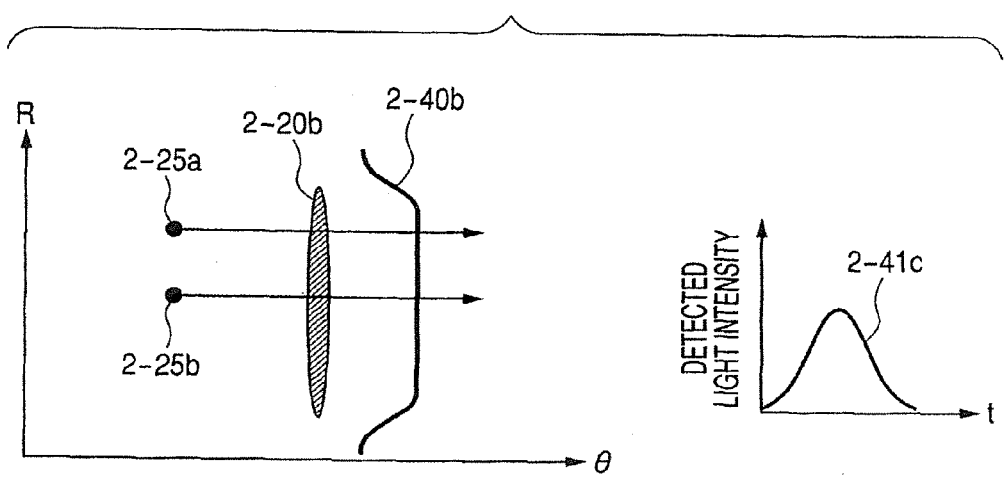
FIG. 23 is an explanatory view showing the relationship between the position through which the defect passes and the generated scattered light intensity when the illumination intensity distribution is uniform.

In the case where the intensity distribution of the beam spot 2-20$a$ has a Gaussian distribution 2-40$a$ as shown in FIG. 22, the scattered light 2-41$a$ is generated by illuminating the defect 2-25$a$ on the beam spot 2-20$a$, and the scattered light 2-41$b$ which is larger than the scattered light 2-41$a$ is generated by illuminating the defect 2-25$b$. In the right side drawing of FIG. 22, y-axis is detected light intensity, and x-axis is time (t). In the case where the intensity distribution of the beam spot 2-20$b$ has the uniform distribution 2-40$b$ on the beam spot 2-20$b$ as shown in FIG. 23, the scattered light 2-41$c$ resulting from illumination to either the defect 2-25$a$ or 2-25$b$ on the beam spot 2-20$b$ has substantially the same size. In the right side drawing of FIG. 23, y-axis is detected light intensity, and x-axis is time (t).

The wafer stage which is rotated at high speeds during the inspection generates oscillation both in height and radial directions. So the fluctuation in the sample height and heave occur at high frequency. There may be often the case where the positional relationship between the defect and the beam spot displaces. However, the fluctuation in the detected scattered light intensity resulting from the displacement of the illumination position may be suppressed by allowing the illumination intensity to have the uniform distribution. This makes it possible to improve the repeatability and stability with respect to the defect detection sensitivity and coordinate accuracy.

In the illumination optical system, the line illumination is performed using the beam expander and the cylindrical lens. However, the Wallaston prism may be used to divide the laser beam so that the divided laser beams are arrayed in the radial direction for illumination, thus making the beam spot long enough to illuminate the sample surface.

The process for dividing the laser beam will be described referring to FIG. 24. Generally, the laser beam 2-100 from the laser light source 2 is linearly-polarized. After passing through the beam expander 2-3 and the homogenizer 2-4, the laser beam is circularly polarized by the quarter-wave plate 2-42$a$ so as to be divided into two linearly-polarized beams which is orthogonal with each other at the Wallaston prism 2-43. The divided laser beam is circularly polarized by the quarter-wave plate 2-42$b$ again such that the sample surface is illuminated by the condensing lens 2-44 on the beam spots 2-20$c$ and 2-20$d$. In this way, the long beam spot may be generated by illuminating the sample on the plural arrayed beam spots.

The distance between the thus divided two beam spots may be arbitrarily adjusted, which allows the illumination by overlapping or separating the beam. This makes it possible to adjust the number of illuminations to substantially the same region.

The intensity of the divided laser beam allows the adjustment of the ellipticity of the circular polarization/azimuth of elliptic long axis by controlling the angle defined by the oscillating direction of the linearly polarized laser beam 2-100 and the phase lag axis of the quarter-wave plate 2-42$a$. Illumination intensity of the beam spots 2-20$c$ and 2-20$d$ divided by the Wallaston prism 2-43 may be arbitrarily adjusted by controlling the ellipticity/azimuth of elliptic long axis. This makes it possible to expand the dynamic range of the detectable defect (to be described later). The beam spots 2-20$c$ and 2-20$d$ may be set to substantially the same intensity values or different intensity values.

Figure 24:
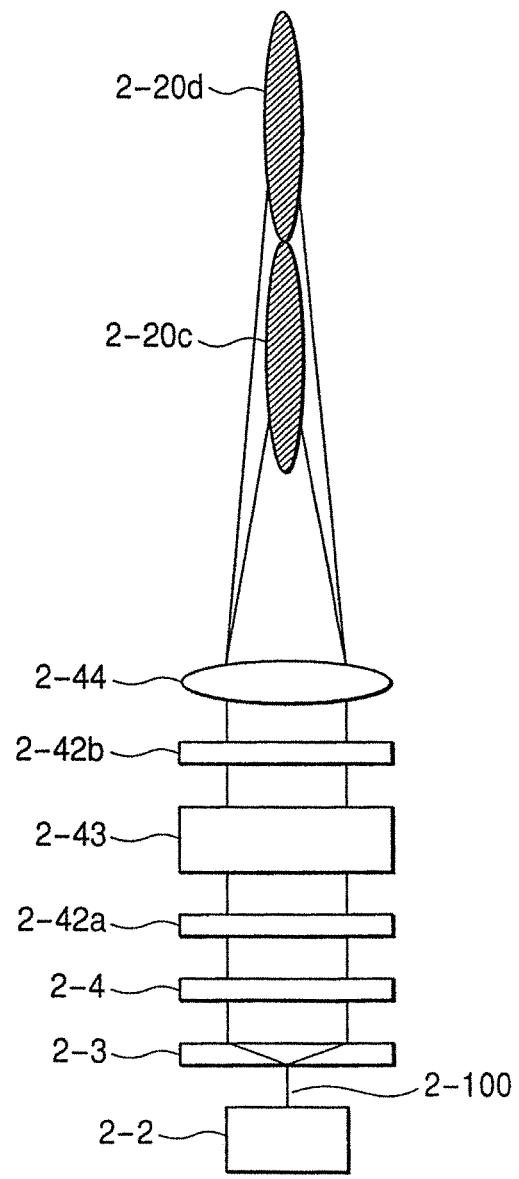
FIG. 24 is an explanatory view of the illumination optical system for dividing the laser beam from the single light source into plural sections, and performing the long illumination by arraying those sections in the radial direction.

In the embodiment shown in FIG. 24, the laser beam is divided into two. However, the laser beam may be divided into four, eight, or more by arranging plural combinations of the Wallaston prisms and the quarter-wave plates to the front of the quarter-wave plate 2-42$b$ and the condensing lens 2-44. The illumination range may be adjusted by controlling each distance among the plural beam spots so as to arbitrarily adjust intensity of the plural laser beams.

Figure 25A:
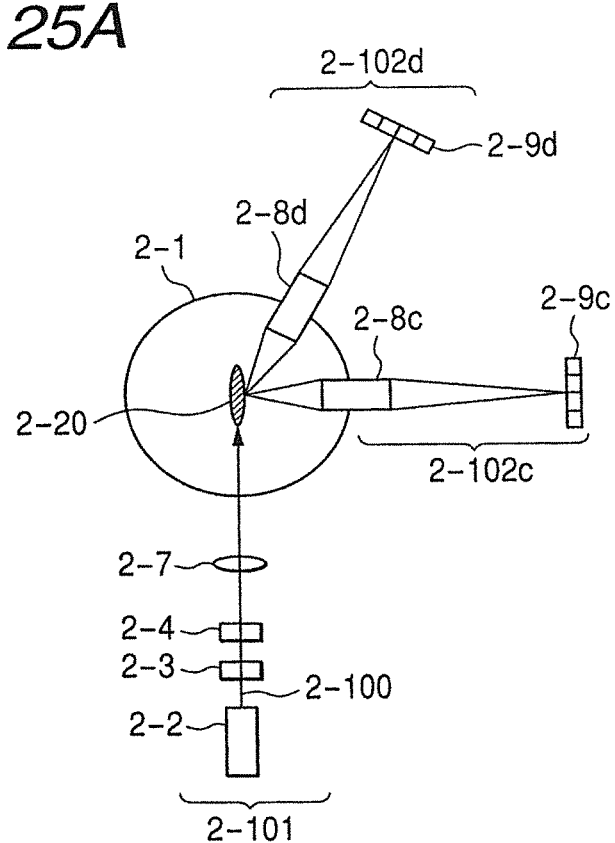
FIGS. 25A and 25B show the process for adding the signals when the photodiode array is employed in the detection optical systems disposed in the plural azimuth directions.

The divided laser beams are arranged in substantially the same direction for illuminating. However, the illumination may be performed in the oblique illumination optical system and the perpendicular illumination optical system simultaneously to array two beam spots. This makes it possible to illuminate the same defect from substantially the perpendicular and oblique directions in the single inspection. The use of the difference in the detected elevation angle/detected azimuth direction improves the defect classification performance In the process for adding the scattered lights in the detection optical system, an example of the detection optical systems in different azimuth directions will be described. Referring to FIG. 25A, two detection optical systems, that is, 2-102$c$ and 2-102$d$ are provided.

Figure 25B:
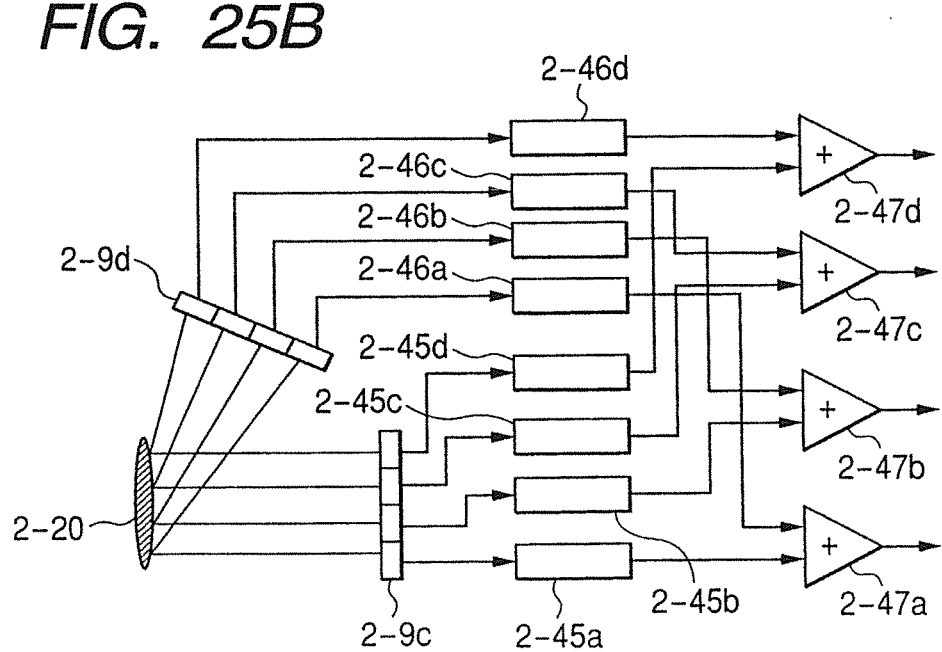

FIG. 25B is an enlarged view showing the beam spot, the photodiode array light receiving section, and the analog circuit. The beam spot 2-20 is divided and detected by the photodiode 2-9c, and the detection signals at the respective light receiving sections are amplified by the corresponding circuits 2-45a to 2-45d for eliminating the noise. Likewise, the beam spot 2-20 is divided and detected by the photodiode 2-9d, and the detection signals at the respective light receiving sections are amplified by the corresponding circuits 2-46a to 2-46d for eliminating the noise. In the adder sections 2-47a to 2-47d, the outputs of the light receiving sections for detecting the scattered lights from substantially the same region on the illuminated portion are added. Outputs of the circuits 2-45a and 2-46a as signals corresponding to substantially the same region on the illuminated portion are added by the adder section 2-47a. Likewise, the outputs of the circuits 2-45b and 2-46b, 2-45c and 2-46c, and 2-45d and 2-46d as signals corresponding to substantially the same region on the illuminated portion are added by the adder sections 2-47b to 2-47d respectively for improving the detection sensitivity.

In the embodiment, four light receiving sections are employed for the photodiode array. However, the number of the light receiving sections is not limited, but may be arbitrarily set. The photodiode array 2-9c does not have to have the same number of the light receiving sections as that of the light receiving sections for the photodiode array 2-9d. If those photodiode arrays use different number of the light receiving sections, signals of the light receiving sections which detect substantially the same region are added.

The number of the detection optical system is not limited to two as described herein. Plural detection optical systems may be provided in plural azimuth/elevation angle directions. If the plural detection optical systems exist, the signals of the light receiving sections which detect substantially the same region in the respective detection optical systems are added.

Figure 26A:
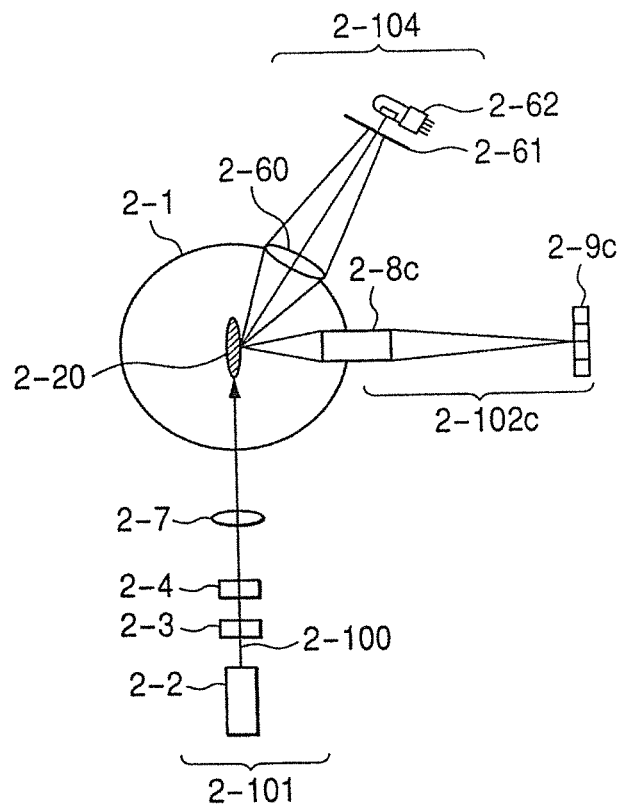
FIGS. 26A and 26B show the process for adding the signal when the photodiode array and PMT are employed in the detection optical systems disposed in the plural azimuth directions.

A method for adding the scattered light in the case where the detection optical systems exist in different azimuth directions will be described taking an example of the detection optical system using the photomultiplier tube (PMT) as the sensor likewise the detection optical system 2-104 shown in FIG. 26A. The detection optical system 2-104 includes a condensing lens 2-60, a pin hole 2-61, and a PMT 2-62. The detection optical system 2-104 uses the pin hole 2-61 to reduce the detection range so as to suppress the noise.

Figure 26B:
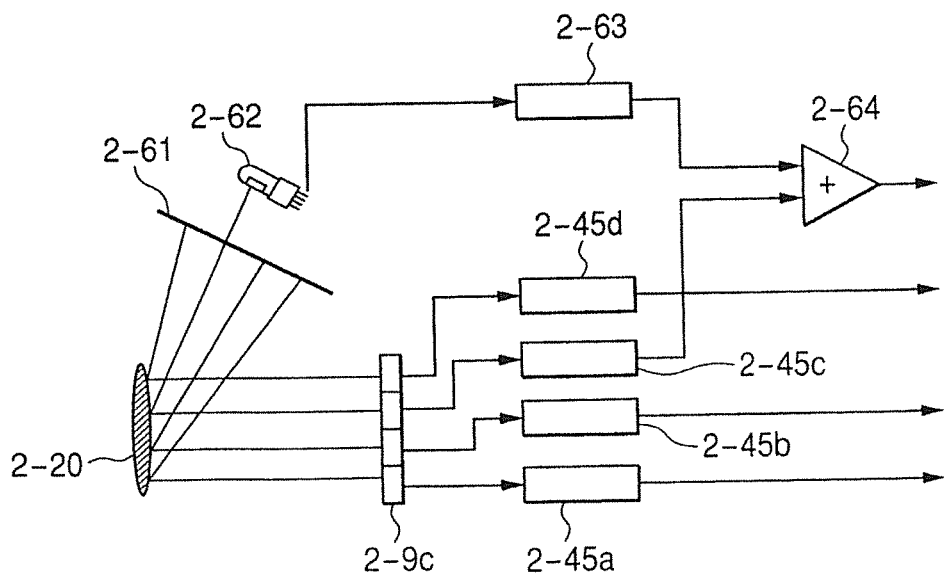

FIG. 26B is an enlarged view of the beam spot, the photodiode array, the PMT, and the analog circuit. The detection signal from the PMT 2-62 is amplified by the circuit 2-63 for eliminating the noise. As outputs of the circuits 2-63 and 2-45c correspond to the signal in substantially the same region of the illuminated portion, the addition is performed by the adder section 2-64 to improve the detection sensitivity. The signals output from the circuits 2-45a, 2-45b, and 2-45d are not added.

The PMT as the point sensor has the high response speed and small data capacity. The PMT may be employed in the section where the high detection sensitivity is not required, thus increasing the inspection speed.

The number of the detection optical systems is not limited to two. Plural systems may be provided in plural azimuth/elevation angle directions. The ratio of the detection optical system provided with the photodiode array to the detection optical system provided with the PMT is not limited to 1:1. The azimuth at which the detection optical system provided with the photodiode array and the detection optical system provided with the PMT are arranged is not limited. Preferably, however, at least one of the photodiode arrays is disposed at the position substantially in parallel with the illuminating direction.

In the inspection method according to the present invention, the same defect is illuminated plural times. Upon the second illumination to the same defect onward, the previous detection signal may be used for feedback. The example for expanding the dynamic range by correcting the sensor sensitivity will be described.

Figure 27A:
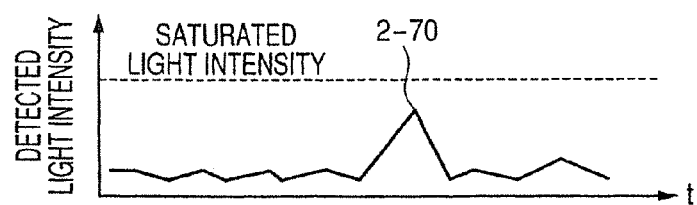
FIGS. 27A and 27B show the detection light intensity when the sensitivity of the light receiving section is different.
Figure 27B:
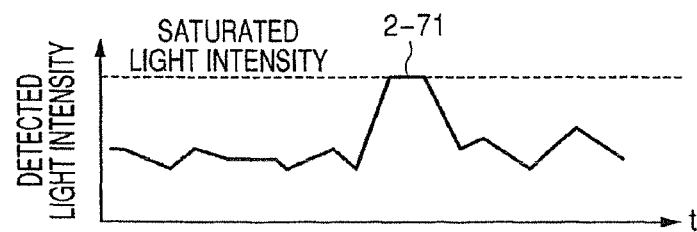
Figure 28A:
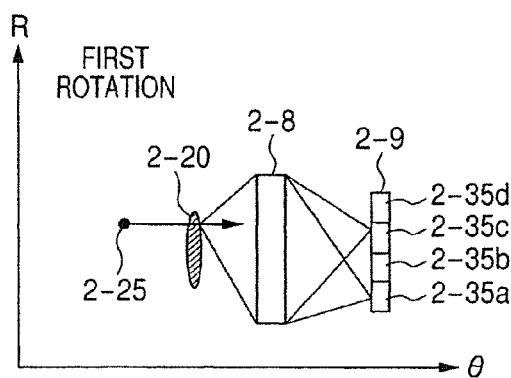
FIGS. 28A and 28B show the process for correcting the sensor sensitivity based on the detection information prior to the rotation.
Figure 28B:
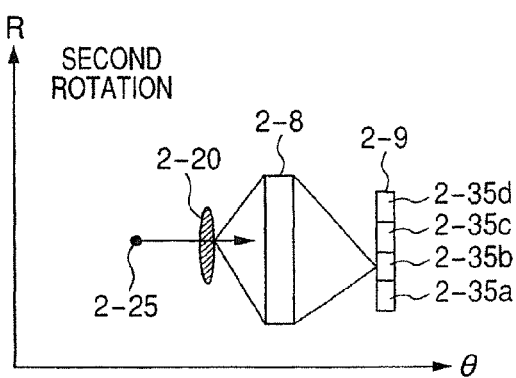

FIGS. 27A and 27B are graphs each having the y-axis as the detected light intensity, and x-axis as the time. Referring to FIG. 27A, the detected light intensity 2-70 is detected without being saturated. Referring to FIG. 27B, the detected light intensity 2-71 is saturated, thus failing to measure the accurate scattered light intensity. In FIGS. 27A and 28B, x-axis is time (t). As the size determination in the defect determination is made based on the level of the detection light intensity, it is important to detect the scattered light while preventing the saturation.

The process for preventing the saturation of the detection light intensity will be described referring to FIGS. 28A and 28B. The scattered light generated when the first illumination to the defect 2-25 is performed on the bema spot 2-20 is detected by the light receiving section 2-35a and 2-35c of the photodiode array 2-9 via the imaging system 2-8. When the resultant detected light intensity is saturated as shown in FIG. 27B, the second illumination is performed by lowering the sensor sensitivity. In the second illumination, the scattered light from the defect 2-25 is detected by the light receiving section 2-35b of the photodiode array 2-9 to allow the scattered light to be detected while preventing the saturation as shown in FIG. 27A.

The sensor sensitivity is corrected by changing the voltage applied to the image intensifier and the multi-anode PMT, changing the sensor storage time, performing the illumination at the changed illumination intensity and the like. The sensor sensitivity may be corrected by adjusting the sensitivity during the inspection as needed. However, such correction may be made by changing the sensitivity for each of the light receiving sections before starting the inspection, or using sensors each having the different sensor sensitivity arrayed preliminarily. In the case where the laser beam is divided by the Wallaston prism so as to be arrayed for illumination to allow each of the divided laser beams to have the different intensity, the divided laser beams are arrayed to generate the line illumination with different illumination intensity distribution in the pseudo manner. This makes it possible to change the detection sensitivity for each of the light receiving sections so as to perform the sensor sensitivity correction.

The process for adding the scattered lights by the signal processor will be described referring to FIG. 29. The graph shown in FIG. 29 has the y-axis as the R (radial) direction and the x-axis as θ (rotation) direction. Coordinates 2-112a to 2-112d represent detection of the same defect. In the present invention, as the same defect is illuminated plural times, the single defect is detected by the same number of times as that of the illumination. For example, the defect coordinates 2-112a, 2-112b, 2-112c, and 2-112d represent detections of the same defect during the first, the second, the third and the fourth illuminations, respectively. Although the coordinates 2-112a to 2-112d represent the same defect, the variation still exists because of errors caused by the fluctuation in the stage height and the illumination position for the respective illuminations. A predetermined region 2-111 is defined by the coordinates 2-110a, 2-110b in the R direction and 2-110c, 2-110d in the θ direction. When the signal detected in the predetermined region is determined as being the one from the same defect so as to be subjected to the integrated processing. As an example of the integrated processing, each gravity center of the defect coordinates of 2-112a to 2-112d is taken to set the final defect coordinate 2-113. Besides the use of the gravity center coordinate as the final defect coordinate, the weighting may be performed so as to set the final defect coordinate. The fluctuation in the coordinate which occurs for each detection is averaged such that the improvement in the coordinate repeatability is expected.

Figure 29:
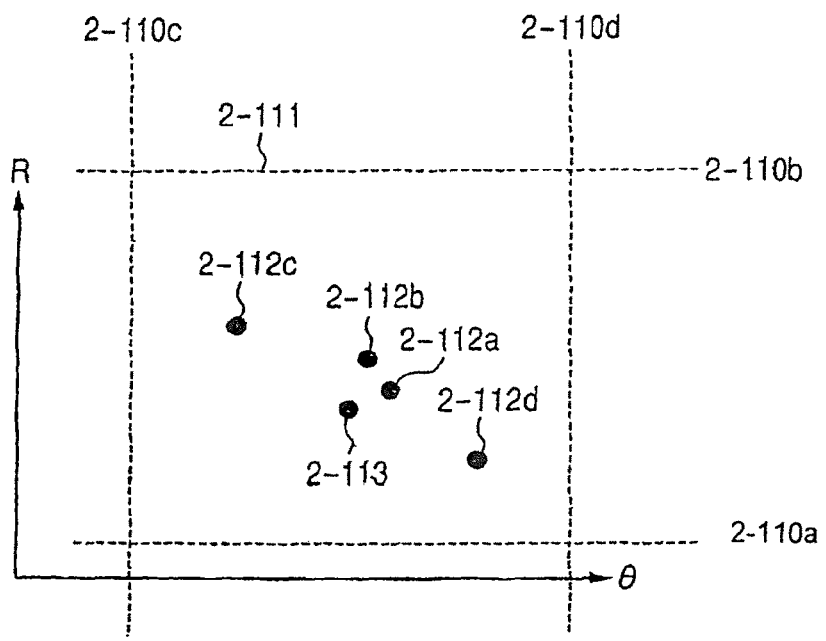
FIG. 29 is an explanatory view representing the coordinate merge process of the signal detected plural times with respect to the same defect.

In the process for adding the scattered lights by the signal processor, the plural detected light intensities detected in the predetermined region 2-111 shown in FIG. 29 are added to set the final detected light intensity, based on which the defect size is determined. Instead of adding the plural detection light intensities to set the final detection light intensity, the average value of the plural detection light intensities may be obtained to be set as the final detection light intensity. If the detected light intensity value is large, the average detected light intensity is obtained rather than performing the adding to suppress the variation in the detected light intensity. This makes it possible to improve the repeatability and stability for determining the defect size. FIG. 29 shows the example where the defect is detected only four times. However, the detection may be performed any number of times.

An example of the inspection method according to the present invention will be described referring to FIGS. 30A and 30B.

Figure 30A:
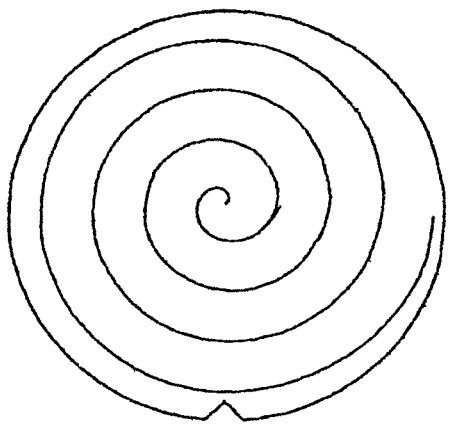
FIGS. 30A and 30B show the difference between the generally employed scanning method and the scanning method according to the present invention.
Figure 30B:
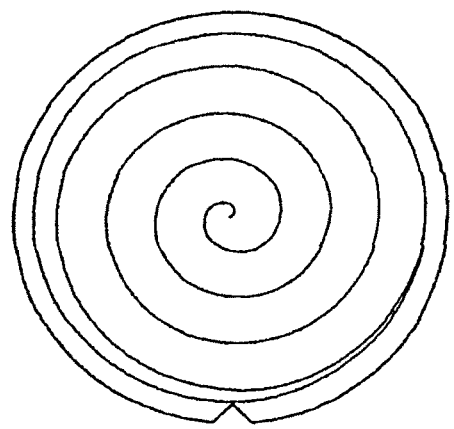

In the generally employed method, the spiral scanning is performed as shown in FIG. 30A. The sample inspection ends when the beam spot reaches the most outer periphery. In the present invention, when the beam spot reaches the most outer periphery, the radial movement of the stage is stopped for performing the concentric scanning as shown in FIG. 30B. This makes it possible for the outer periphery to illuminate substantially the same region plural times likewise the inner periphery, thus preventing deterioration in the detection sensitivity on the outer periphery.

The number of times for illumination on the outer periphery may be arbitrarily set for performing the concentric scanning. On the inner periphery, the number of times for illumination to substantially the same region is determined based on the relationship between the beam spot length and the feed pitch length. However, the number of times for illuminating the outer periphery does not have to be set to the same number of times for illuminating the inner periphery. It may be increased to be larger than that for illuminating the inner periphery.

Figure 31:
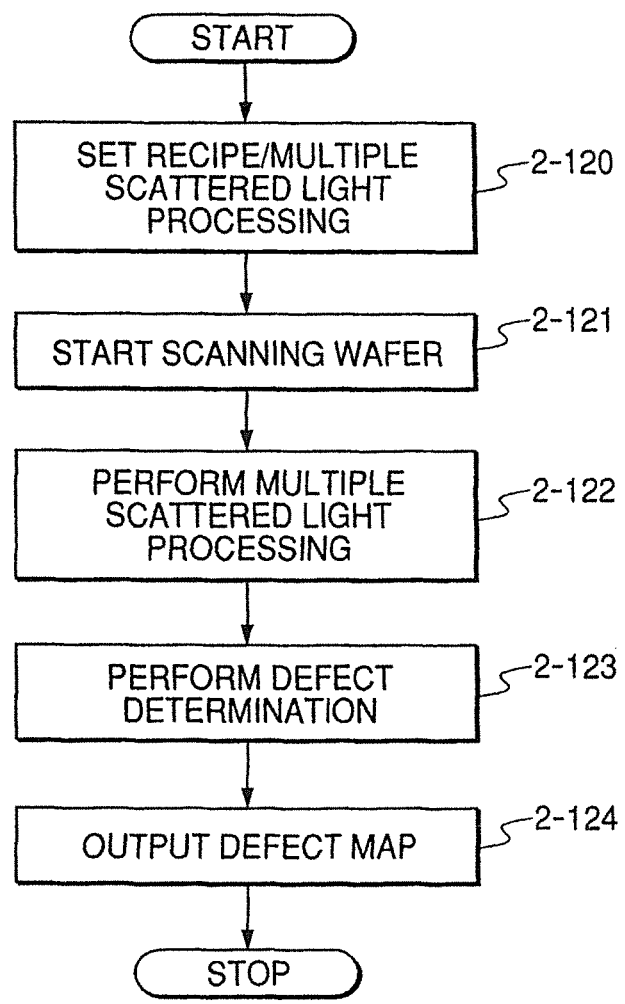
FIG. 31 is a flowchart showing the process for detecting the defect in the inspection apparatus.

The routine for detecting the defect will be described referring to FIG. 31. The recipe is set to determine the inspection conditions such as the illumination direction and the sensor sensitivity in step 2-120. The process in step 2-120 includes the step of setting the processing performed with respect to the beam spot length, the feed pitch and the detected scattered light. The wafer scanning is started in step 2-121, and the detected scattered light is subjected to the signal processing set by the recipe in step 2-122. The defect determination is performed based on the processed signal in step 2-123. Then the defect map is displayed in step 2-124.

Figure 32:
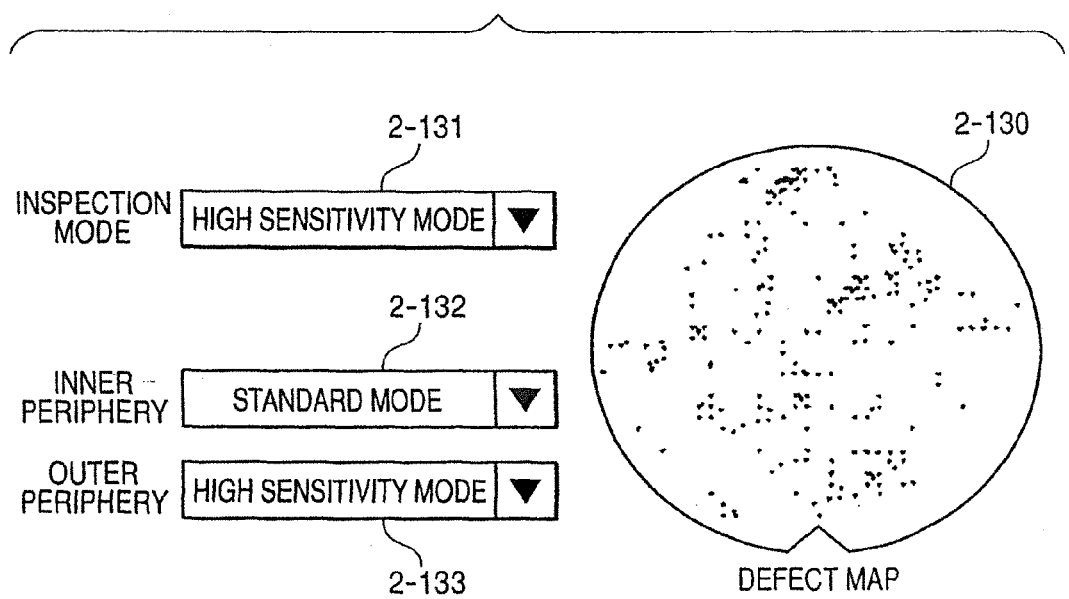
FIG. 32 is a view showing an example of GUI.

FIG. 32 shows an example of the GUI which includes a defect map 2-130 displayed after the end of the inspection, and a sub-window for setting the inspection mode before starting the inspection. The defect map is displayed based on the defect signal loaded upon the inspection and the coordinates. The inspection mode 2-131 may be selected through the direct inputting or selection from the pull-down menu. The number of times for illuminating the same defect in the single inspection does not have to be the same. For example, on the inner periphery of the sample, the inspection mode is selected to the standard mode (2-132), and on the outer periphery of the sample, the inspection mode is selected to the high sensitivity mode (2-133). In the high sensitivity mode, the feed pitch is decreased, and the number of times for illumination is increased to improve the detection sensitivity.

In the embodiment of the present invention, the same defect is illuminated plural times in the single inspection, and the scattered lights generated plural times are added to improve the detection sensitivity. The use of the photodiode array with the plural pixels allows the inspection without deteriorating the throughput. The embodiment of the present invention provides the inspection method and the inspection apparatus, realizing both the improvement in the detection sensitivity and the increase in the throughput. The information to be illuminated and detected plural times is used to expand the dynamic range and to improve accuracy in the coordinate and the defect size determination.

The defect inspection method and the defect inspection apparatus improve the detection sensitivity while suppressing increase in the temperature of the sample surface.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What we claim is:

1. A surface defect inspection apparatus comprising:
    an illumination optical system that linearly irradiates a beam on a surface of an inspection sample to form a linear illumination region on the inspection sample surface, wherein the linear illumination optical system is configured to irradiate the beam at a same region of the inspection sample surface a plural number of times,
    a stage that holds an inspection sample and configured to be moved in a longitudinal direction of the linear illumination region at a feed pitch shorter than a longitudinal length of the linear illumination region, the feed pitch being variable; and
    at least one detection optical system that detects scattered lights scattered plural times from the linear illumination region on the inspection sample surface,
    wherein the at least one detection optical system includes a focusing system and a multi-pixel sensor array, and is located perpendicular to a longitudinal direction of the linear illumination region.

2. A surface defect inspection apparatus according to claim 1,
    wherein the multi-pixel sensor array comprises a photodiode array.

3. surface defect inspection apparatus according to claim 1,
    wherein the focusing system of the at least one detection optical system is configured to focus the plurality of scattered lights to the multi-pixel sensor array, and the multi-pixel sensor array is configured to detect the scattered lights.

4. A surface defect inspection apparatus according to claim 1,
    wherein the illumination optical system is configured to irradiate beams onto the surface of the inspection sample from plural directions.

5. A surface defect inspection apparatus according to claim 1,
    wherein the apparatus includes a plurality of detection optical systems.

6. A surface defect inspection apparatus according to claim 1, wherein a processing unit is configured to process the electrical signal and to classify kinds of defects based on processing by the processing unit.

7. A surface defect inspection apparatus according to claim 1,
further comprising means for converting a plurality of scattered lights detected by the at least one detection optical system into a plurality of electric signals,
wherein the plurality of electric signals are configured to be used to classify defects.

8. A surface defect inspection method comprising:
a step of linearly irradiating a beam on a surface of an inspection sample a plural number of times on a same region of the surface of the inspection sample to form a linear illumination region on the inspection sample surface,
a step of holding the inspection sample by a stage and moving the inspection sample in a longitudinal direction of the linear illumination region at a feed pitch shorter than a longitudinal length of the linear illumination region, the feed pitch being variable, and
a step of detecting scattered lights scattered plural times from the linear illumination region on the inspection sample surface by at least one detection optical system,
wherein the at least one detection optical system includes a focusing system and a multi-pixel sensor array, and is located perpendicular to the longitudinal direction of the linear illumination region.

9. A surface defect inspection method according to claim 8, wherein the multi-pixel sensor array is comprised of a photodiode array.

10. A surface defect inspection method according to claim 8, further comprising focusing, via the focusing system of the at least one detection optical system, the plurality of scattered lights to the multi-pixel sensor array, and detecting the scattered lights with the multi-pixel sensor array.

11. A surface defect inspection method according to claim 8,
further comprising irradiating, via the illumination optical system, beams onto the surfaces of the inspection sample from plural directions.

12. A surface defect inspection method according to claim 8,
wherein a plurality of detection optical systems are provided.

13. A surface defect inspection method according to claim 8, further comprising processing, via a processing unit, the electrical signal and classifying kinds of defects based on processing by the processing unit.

14. A surface defect inspection method according to claim 8, further comprising converting a plurality of scattered lights detected by the at least one detection optical system to a plurality of electric signals, and classifying defects based on the plurality of electric signals.

* * * * *